US012577771B2

(12) United States Patent
Dholakia et al.

(10) Patent No.: US 12,577,771 B2
(45) Date of Patent: Mar. 17, 2026

(54) DEVICE, SYSTEM AND METHOD FOR MOUNTING AN ACCESSORY TO A TOILET

(71) Applicant: Throne, Inc., Austin, TX (US)

(72) Inventors: Devan Dholakia, Austin, TX (US);
Timothy Blumberg, Austin, TX (US);
Randall Scott Hickle, II, Austin, TX (US)

(73) Assignee: Throne, Inc., Austin, TX (US)

( * ) Notice: Subject to any disclaimer, the term of this patent is extended or adjusted under 35 U.S.C. 154(b) by 0 days.

(21) Appl. No.: 19/260,766

(22) Filed: Jul. 7, 2025

(65) Prior Publication Data

US 2025/0333943 A1     Oct. 30, 2025

Related U.S. Application Data

(63) Continuation-in-part of application No. 19/061,676, filed on Feb. 24, 2025.

(60) Provisional application No. 63/556,664, filed on Feb. 22, 2024.

(51) Int. Cl.
*E03D 9/00*      (2006.01)
*A61B 5/00*      (2006.01)

(52) U.S. Cl.
CPC .............. *E03D 9/00* (2013.01); *A61B 5/0077* (2013.01)

(58) Field of Classification Search
CPC ........................................................ E03D 9/02
See application file for complete search history.

(56) References Cited

U.S. PATENT DOCUMENTS

| | | | |
|---|---|---|---|
| 9,702,132 B2 * | 7/2017 | Chimene | .............. F21V 33/004 |
| 10,575,830 B2 | 3/2020 | Attar | |
| 11,129,599 B2 | 9/2021 | Attar | |
| 11,467,091 B2 | 10/2022 | Attar et al. | |
| 11,561,181 B2 | 1/2023 | Attar et al. | |
| 11,786,224 B2 | 10/2023 | Attar | |
| 11,971,356 B2 | 4/2024 | Attar et al. | |
| 12,390,200 B2 | 8/2025 | Attar | |
| 12,392,313 B2 | 8/2025 | Attar et al. | |

(Continued)

FOREIGN PATENT DOCUMENTS

| | | |
|---|---|---|
| CN | 110461219 | 11/2019 |
| WO | WO-2016135735 | 9/2016 |

(Continued)

OTHER PUBLICATIONS

OutSense.com [online], "Transforming human waste into lifesaving medical insights", retrieved on Jul. 9, 2025, URL<https://outsensediagnostics.com/>, 14 pages.

(Continued)

*Primary Examiner* — Christine J Skubinna
(74) *Attorney, Agent, or Firm* — Strategic Patents, P.C.

(57) ABSTRACT

A device can be mounted to a rim of a bowl of a toilet. The device includes a front body located on an exterior of the bowl, and a rear body located in an interior of the bowl. In addition, a bridge couples the front body to the rear body at a fixed distance therebetween such that the device, when mounted, straddles the rim. The device also has a flexible member located between the front body and the rear body. The flexible member adaptably accommodates a width of the rim that is less than the fixed distance to define a device width, to removably secure and retain the device on the rim.

22 Claims, 21 Drawing Sheets

(56) References Cited

U.S. PATENT DOCUMENTS

| | | | | |
|---|---|---|---|---|
| 2012/0266920 A1* | 10/2012 | Burt | ......................... | E03D 9/032 |
| | | | | 4/224 |
| 2017/0049326 A1 | 2/2017 | Alfano et al. | | |
| 2019/0008439 A1 | 1/2019 | Sageder et al. | | |
| 2019/0177960 A1* | 6/2019 | Sonovani | .................. | E03D 9/02 |
| 2021/0203520 A1 | 7/2021 | Rexach et al. | | |
| 2023/0121436 A1 | 4/2023 | Attar et al. | | |
| 2023/0284845 A1* | 9/2023 | Shimada | ................ | A47K 13/24 |
| 2023/0359910 A1 | 11/2023 | Bonutti et al. | | |
| 2023/0413408 A1* | 12/2023 | Alexander | ................ | A61L 2/10 |
| | | | | D26/61 |
| 2025/0057455 A1* | 2/2025 | Pons | .................... | A61B 10/007 |
| 2025/0268476 A1 | 8/2025 | Hickle, II et al. | | |

FOREIGN PATENT DOCUMENTS

| | | | |
|---|---|---|---|
| WO | WO2021216740 A1 | 10/2021 | |
| WO | WO-2025179279 | 8/2025 | |

OTHER PUBLICATIONS

Amazon.com [online], "LooLoo 3.0 Touch Free Toilet Freshener Automatic Air Freshener Spray for Bathroom Starter Kit with Light and Deodorizer, Bathroom Spray—Citrus Fresh", retrieved on Jul. 9, 2025, URL<https://www.amazon.com/LooLoo-Freshener-Automatic-Bathroom-Deodorizer/dp/B0F56M2VD3/ref=sr_1_7?crid=NVJA9OR6JT2I&dib=eyJ2ljoiMSJ9.L3wtaGadm0S3GhjbcO5x9orypkZgX7d51ee0FUGRQzEbo87e_g2t825DnxEJ1_nVYeNMxTtet_OKL-xyvlErZU1Z-W0g95itsEfeFcZ6GPEzsmxuDkHVWkpdNPJVRw15bb9OOY02IQ2IGqTs95bAbobG0pJTo8VssjopJP clMQjK.

US/ISA, , "PCT Application No. PCT/US23/83549 International Search Report and Written Opinion dated Apr. 25, 2025", , 13 pages.

USPTO, , "U.S. Appl. No. 19/061,676 Final Office Action mailed Sep. 30, 2025", , 9 Pages.

USPTO, , "U.S. Appl. No. 19/061,676 Non-Final Office Action mailed May 15, 2025", , 9 Pages.

* cited by examiner

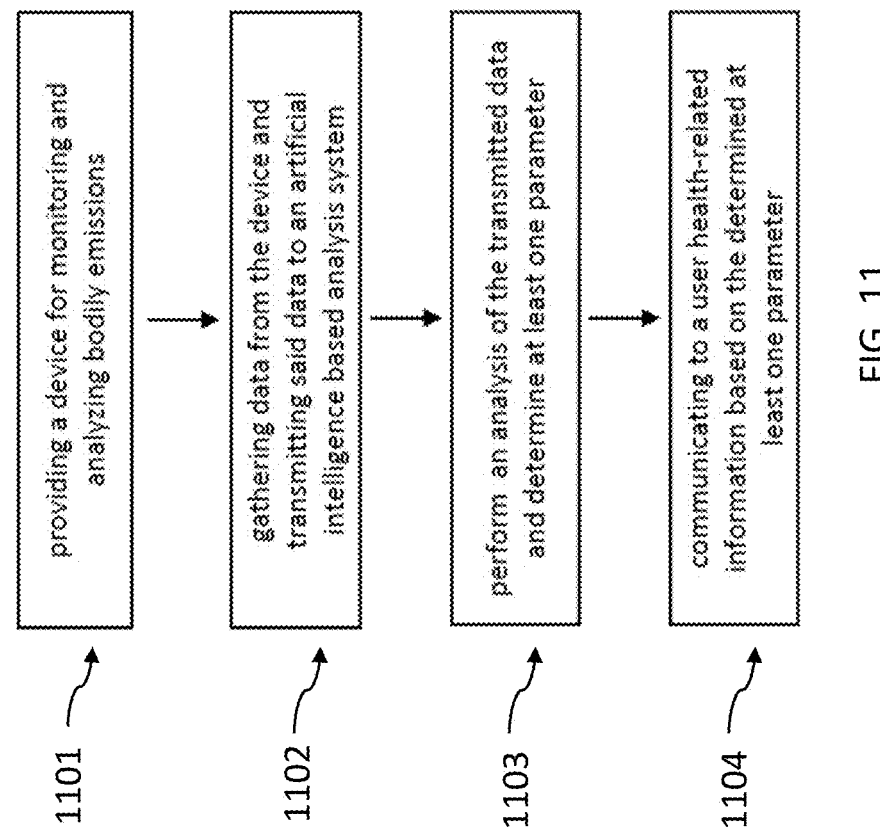

1101    providing a device for monitoring and analyzing bodily emissions 1102    gathering data from the device and transmitting said data to an artificial intelligence based analysis system 1103    perform an analysis of the transmitted data and determine at least one parameter 1104    communicating to a user health-related information based on the determined at least one parameter

FIG. 11

DEVICE, SYSTEM AND METHOD FOR MOUNTING AN ACCESSORY TO A TOILET

CROSS-REFERENCE TO RELATED APPLICATIONS

This application is a continuation-in-part (CIP) of and claims the benefit of and priority to U.S. patent application Ser. No. 19/061,676, filed Feb. 24, 2025, which claims priority to and the benefit of U.S. Prov. Patent App. No. 63/556,664, filed Feb. 22, 2024, each of which is incorporated herein by reference in its entirety.

TECHNICAL FIELD

This disclosure relates to a toilet accessory and, in particular, to a device, system and method for mounting an accessory to a toilet.

BACKGROUND

Health monitoring systems that are user friendly and readily available to an individual, without requiring a doctor's visit, have become increasingly appealing, particularly in today's society that focuses heavily on wellness, preventive health, and longevity. With an overburdened and cumbersome healthcare system, individuals desire to have at-home options for easily monitoring various aspects of their health.

Therefore, there is a need for at-home devices that an individual can utilize to monitor and analyze various aspects of their health in real time, without the need for doctor's visits and laboratory testing. A variety of health-related or nutrition-related parameters can be analyzed based on a user's excreta or urine. As such, there is a need for practically and effectively mounting, to a toilet, a device or system that allows an individual to obtain health related metrics from their routine bodily emissions, in real time, in the privacy of their own home.

SUMMARY

Embodiments of a device, system and method for mounting an accessory to a toilet are disclosed. For example, the device can be mounted to a rim of a bowl of a toilet. The device can include a front body configured to be located on an exterior of the bowl, and a rear body configured to be located in an interior of the bowl. In addition, a bridge can couple the front body to the rear body at a fixed distance therebetween such that the device, when mounted, is configured to straddle the rim. The device also has a flexible member located between the front body and the rear body. The flexible member is configured to adaptably accommodate a width of the rim that is less than the fixed distance to define a device width, to removably secure and retain the device on the rim.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. For a detailed description of example embodiments, reference will now be made to the accompanying drawings.

FIG. 11 generally illustrates methods related to monitoring and analysis of bodily emissions, in accordance with embodiments of the present disclosure.

NOTATION AND NOMENCLATURE

Figure 1:
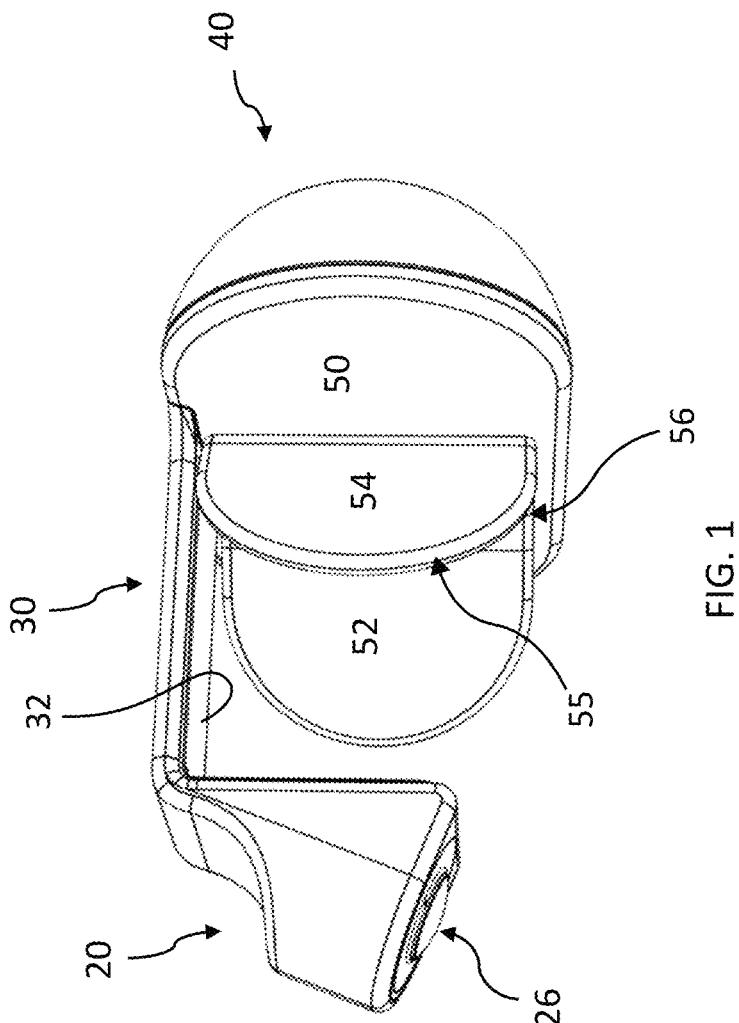
FIG. 1 generally illustrates a perspective view of a device for monitoring and analysis of bodily emissions, in accordance with embodiments of the present disclosure.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

The terminology used herein is for describing particular example embodiments only, and is not intended to be limiting. As used herein, the singular forms "a," "an," and "the" may be intended to include the plural forms as well, unless the context clearly indicates otherwise. The method steps, processes, and operations described herein are not to be construed as necessarily requiring their performance in the particular order discussed or illustrated, unless specifically identified as an order of performance. It is also to be understood that additional or alternative steps may be employed.

The term "about" is used in conjunction with numeric values to include normal variations in measurements as expected by persons skilled in the art, and is understood to have the same meaning as "approximately" and to cover a typical margin of error, such as ±15%, ±10%, ±5%, ±1%, ±0.5%, or even ±0.1% of the stated value. The term "about" also encompasses amounts that differ due to different equilibrium conditions for a composition resulting from a particular initial composition. Whether or not modified by the term "about," the claims include equivalents to the quantities.

It should be noted that, as used in this specification and the appended claims, the singular forms "a," "an," and "the" include plural referents unless the content clearly dictates otherwise. Thus, for example, reference to a composition containing "a compound" includes having two or more compounds that are either the same or different from each other. It should also be noted that the term "or" is generally employed in its sense including "and/or" unless the content clearly dictates otherwise. As used herein, "and/or" refers to and encompasses any and all possible combinations of one or more of the associated listed items, as well as the lack of combinations when interpreted in the alternative ("or").

In the interest of brevity and conciseness, any ranges of values set forth in this specification contemplate all values within the range and are to be construed as support for claims reciting any sub-ranges having endpoints that are real number values within the specified range in question. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

The term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

The term "comprise," "comprises," and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "increased," "enhance," "enhanced," "enhancing," and "enhancement" (and grammatical variations thereof) describe an elevation of at least about 1%, 5%, 10%, 15%, 25%, 50%, 75%, 100%, 150%, 200%, 300%, 400%, 500% or more as compared to a control.

As used herein, the terms "reduce," "reduced," "reducing," "reduction," "diminish," and "decrease" (and grammatical variations thereof), describe, for example, a decrease of at least about 1%, 5%, 10%, 15%, 20%, 25%, 35%, 50%, 75%, 80%, 85%, 90%, 95%, 97%, 98%, 99%, or 100% as compared to a control. In particular embodiments, the reduction can result in no or essentially no (i.e., an insignificant amount, e.g., less than about 10% or even 5% or even 1%) detectable activity or amount.

The terms "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the present disclosure.

The terms first, second, third, etc. may be used herein to describe various elements, components, regions, layers and/or sections; however, these elements, components, regions, layers and/or sections should not be limited by these terms. These terms may be only used to distinguish one element, component, region, layer, or section from another region, layer, or section. Terms such as "first," "second," and other numerical terms, when used herein, do not imply a sequence or order unless clearly indicated by the context. Thus, a first element, component, region, layer, or section discussed below could be termed a second element, component, region, layer, or section without departing from the teachings of the example embodiments. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

Spatially relative terms, such as "inner," "outer," "beneath," "below," "lower," "above," "upper," "top," "bottom," "inside," "outside," "contained within," "superimposing upon," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

DETAILED DESCRIPTION

The following discussion is directed to various embodiments of the present disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Disclosed herein are devices, systems and methods for monitoring and analysis of bodily emissions, emitted from a user during toilet use. The bodily emissions include excreta, urine, and menses. In one embodiment, a device is disclosed for monitoring and analysis of bodily emissions emitted from a user, the device comprising an image capturing apparatus, at least one light emission source, at least one sensor, and a processing device configured to gather data from the image capturing apparatus and/or the at least one sensor and transmit said data to an artificial intelligence based analysis system. The artificial intelligence based analysis system is configured to perform an analysis of the transmitted data, and determine at least one parameter from the performed analysis.

In an embodiment, the determined parameter comprises health related information derived from the user's excretions and/or urine. The health related information can include the user's bowel movement characteristics, hydration levels, substance detection, blood detection in stool or urine, fiber content detection in stool, allergen detection, biomarker detection, hormone detection, bacterial or fungal organism detection.

The determined parameter and/or health related information is then communicated to the user through a visual interface, such as mobile electronic device, a phone, a tablet, a computing device, a wearable (e.g. watch), a spatial or augmented reality computing device, and the like.

The device, as shown in FIGS. 1-3 and FIGS. 4A-4C is mountable on a user's toilet and can be positioned on or under the toilet seat, such that when a user is seated, the user is not in contact with the device. For example, the device may be mounted on a rim portion on either side or front of the toilet bowl, such that certain sensors are positioned internally in the toilet bowl where measurable parameters of excreta can be obtained. Other embodiments of the device may position the device support structures outside and completely unattached to the toilet such as by allowing the device to be freestanding on the floor next to or behind the toilet with sensors passing through the air space between the toilet bowl upper rim and the underside of the toilet seat so that measurable parameters inside the toilet bowl can be obtained. These measurable parameters include still and video images of stool and urine in a range of resolutions taken with lighting illumination that include multiple wavelengths along the electromagnetic spectrum including infrared, visible, and ultraviolet light. Other measurable parameters include soundwaves.

In one embodiment, shown in FIG. 1, the device 100 has a front portion 40, and a back portion 20. The back portion and front portion are connected via bridge 30. Bridge 30 comprises an underside flattened portion of the device that can be placed on top of a rim portion of a toilet, when mounted. The front portion 40 of the device includes a rear surface 50 that is coupled (e.g., fastened) to two attachment arms 52 and 54. Attachment arms 52, 54 are designed to interface with an outer side surface of a toilet and provide a securing mechanism for device 100 to be securely positioned on the toilet. The back portion 20 of device 100 faces internally into a toilet bowl, while the front portion 40 is positioned and faces externally away from the bowl.

Figure 3:
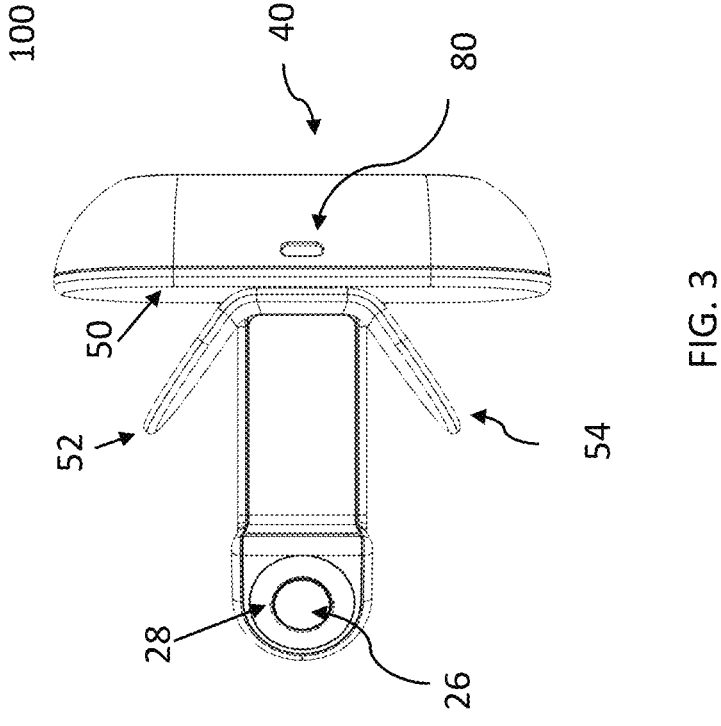
FIG. 3 generally illustrates a bottom view an embodiment of a device for monitoring and analysis of bodily emissions, in accordance with embodiments of the present disclosure.
Figure 2:
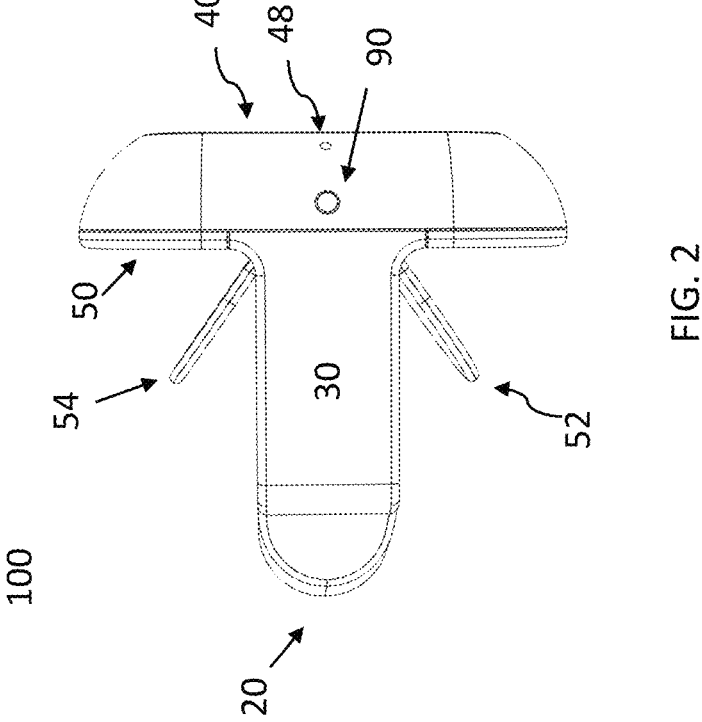
FIG. 2 generally illustrates a top view an embodiment of a device for monitoring and analysis of bodily emissions, in accordance with embodiments of the present disclosure.

FIGS. 2 and 3 show a top view and bottom view of device 100, respectively. In FIG. 2 the configuration and angle of the two attachment arms 52 and 54 are shown, as protruding away from a back surface of the front potion 40, at about a 45 degree angle with respect to back surface 50. The attachment arms 52 and 54 are configured to be flexible and moveable. This angled configuration shown in FIGS. 2 and 3 is present when the device is not yet attached to a toilet. When the device is mounted on a toilet rim, attachment arms 52 and 54, due to their flexible design and material, may adjust and flex closer towards back surface 50, in a variety of angles with respect to back surface 50. The magnitude of the extension of attachment arms 52 and 54 will depend on the thickness of the toilet rim.

Figures 4A, 4B, 4C:
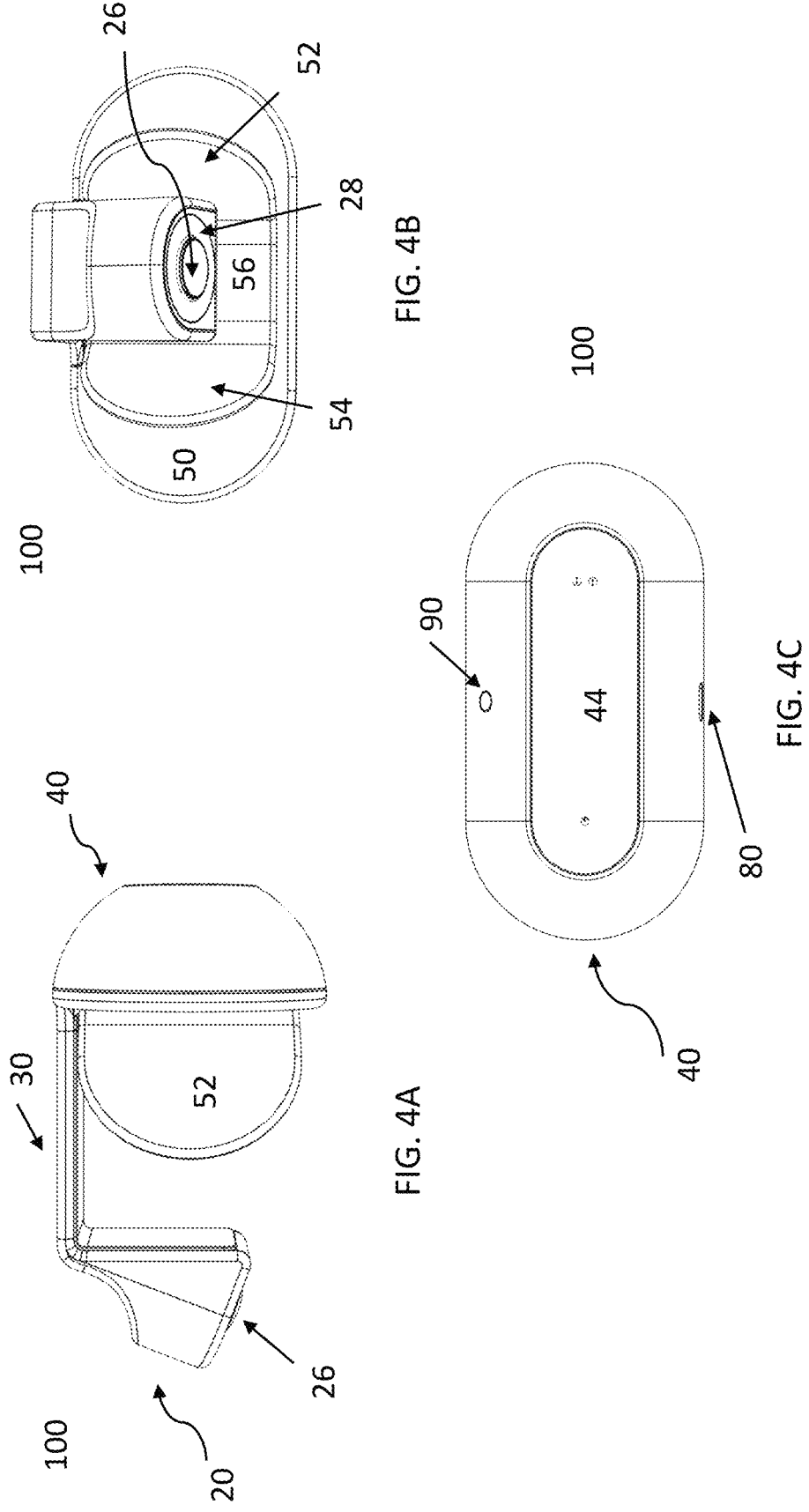
FIG. 4A generally illustrates a side view an embodiment of a device for monitoring and analysis of bodily emissions, in accordance with embodiments of the present disclosure.
FIG. 4B generally illustrates a rear view an embodiment of a device for monitoring and analysis of bodily emissions, in accordance with embodiments of the present disclosure.
FIG. 4C generally illustrates a front view an embodiment of a device for monitoring and analysis of bodily emissions, in accordance with embodiments of the present disclosure.
Figure 5:
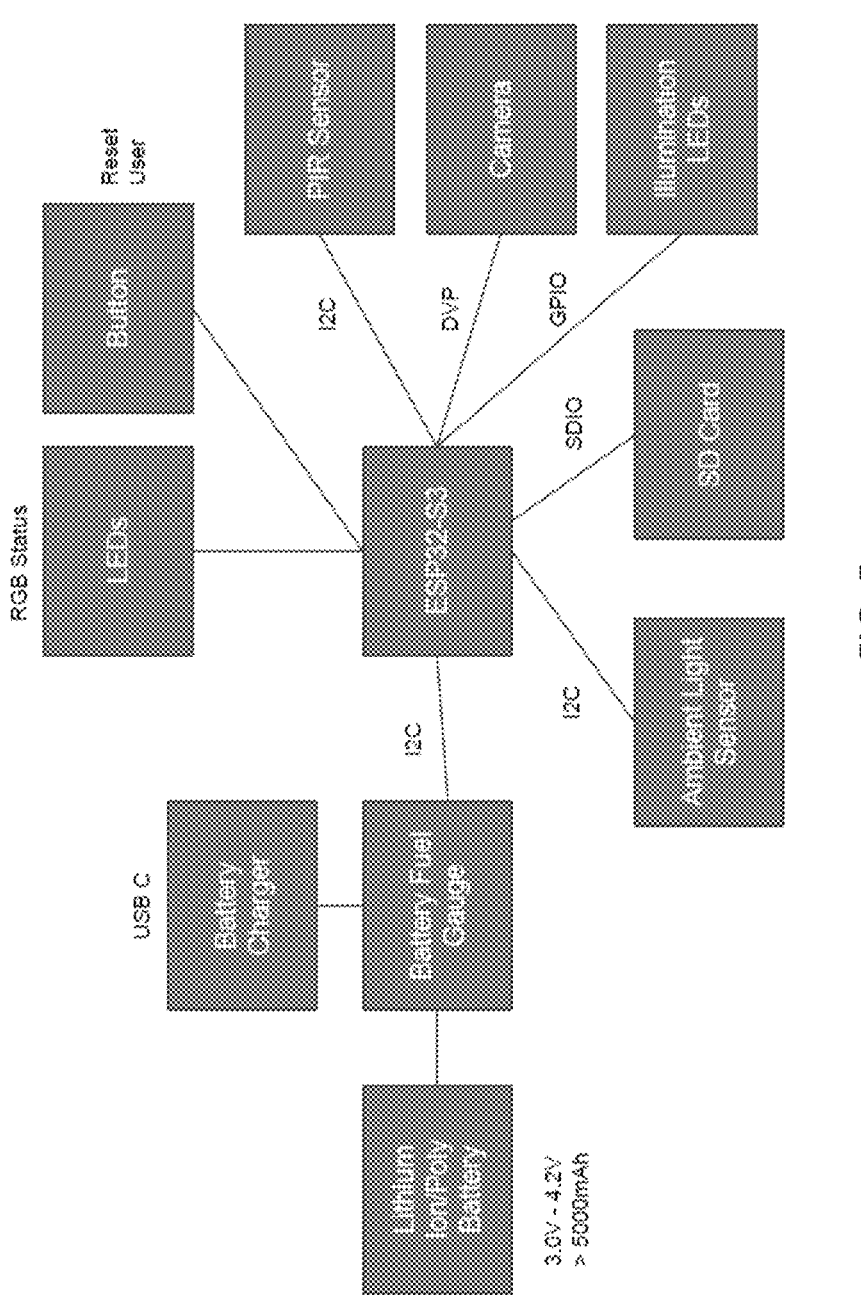
FIG. 5 generally illustrates a block diagram of components of a device for monitoring and analysis of bodily emissions, in accordance with embodiments of the present disclosure.
Figure 6:
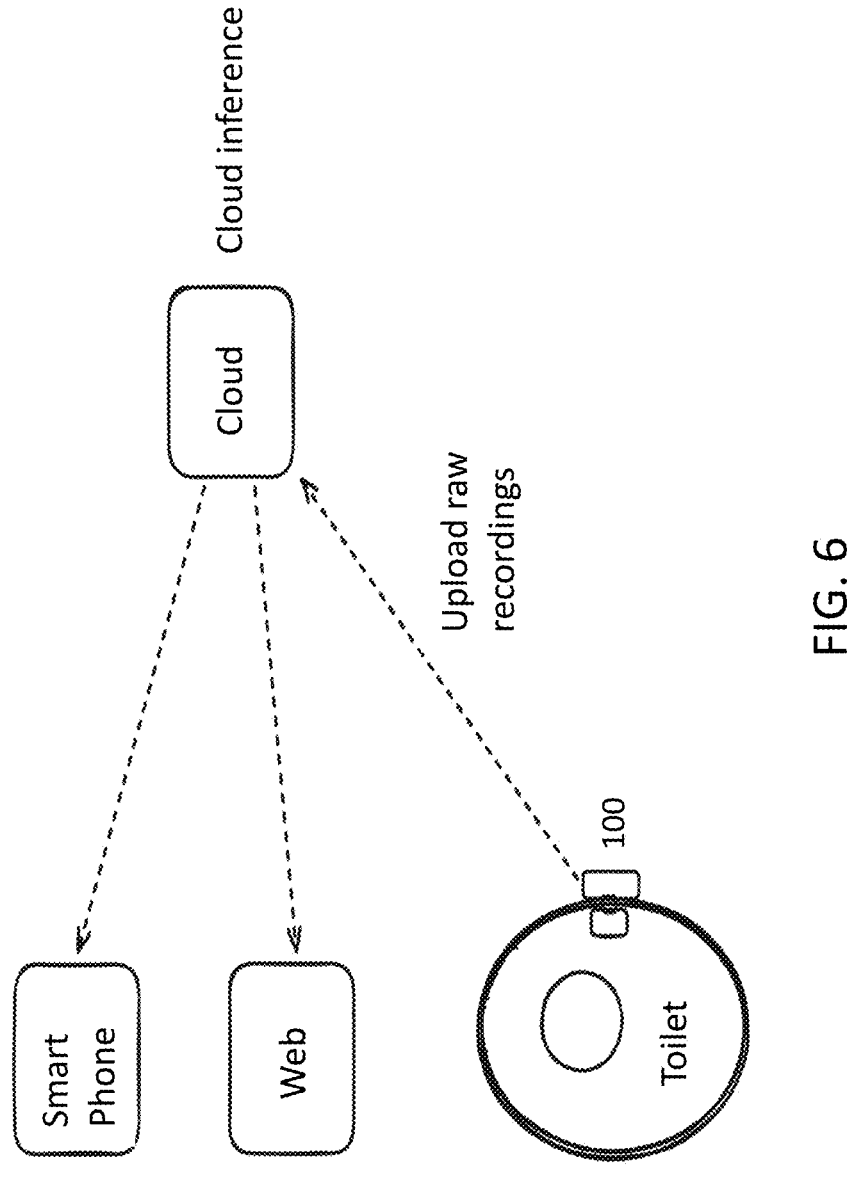
FIG. 6 generally illustrates a schematic of a system for monitoring and analysis of bodily emissions, in accordance with embodiments of the present disclosure.
Figure 7:
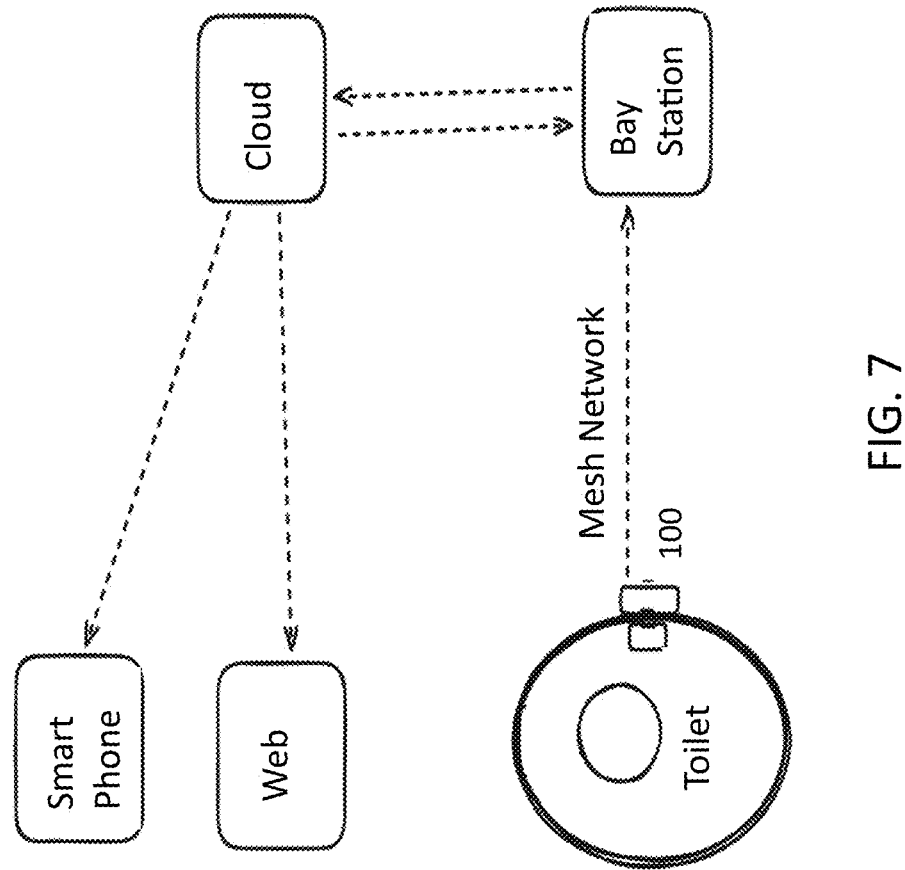
FIG. 7 generally illustrates a schematic of a system for monitoring and analysis of bodily emissions, in accordance with additional embodiments of the present disclosure.
Figure 8:
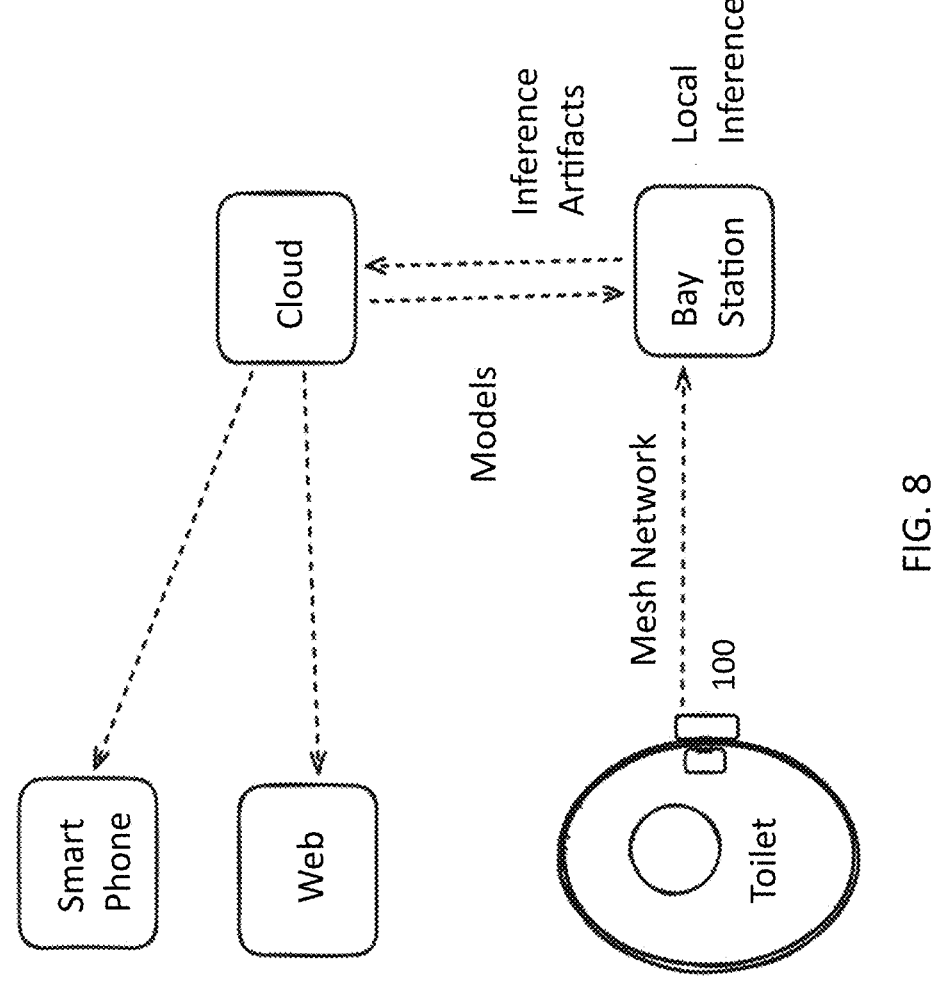
FIG. 8 generally illustrates a schematic of a system for monitoring and analysis of bodily emissions, in accordance with additional embodiments of the present disclosure.
Figure 9:
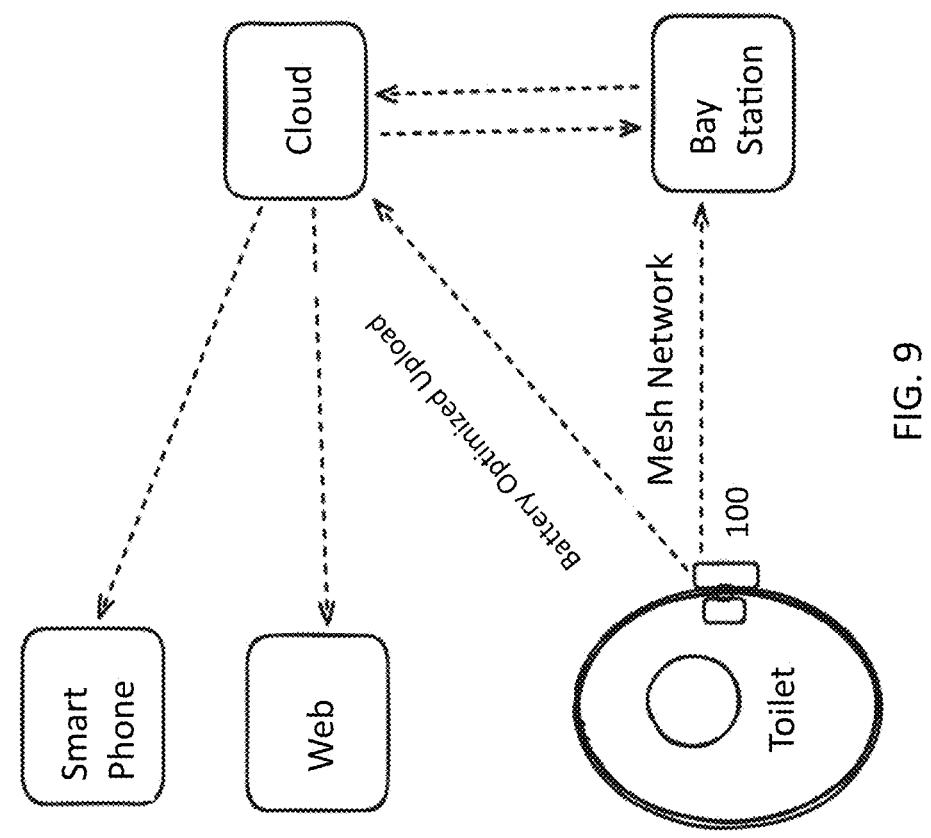
FIG. 9 generally illustrates a schematic of a system for monitoring and analysis of bodily emissions, in accordance with additional embodiments of the present disclosure.
Figure 10:
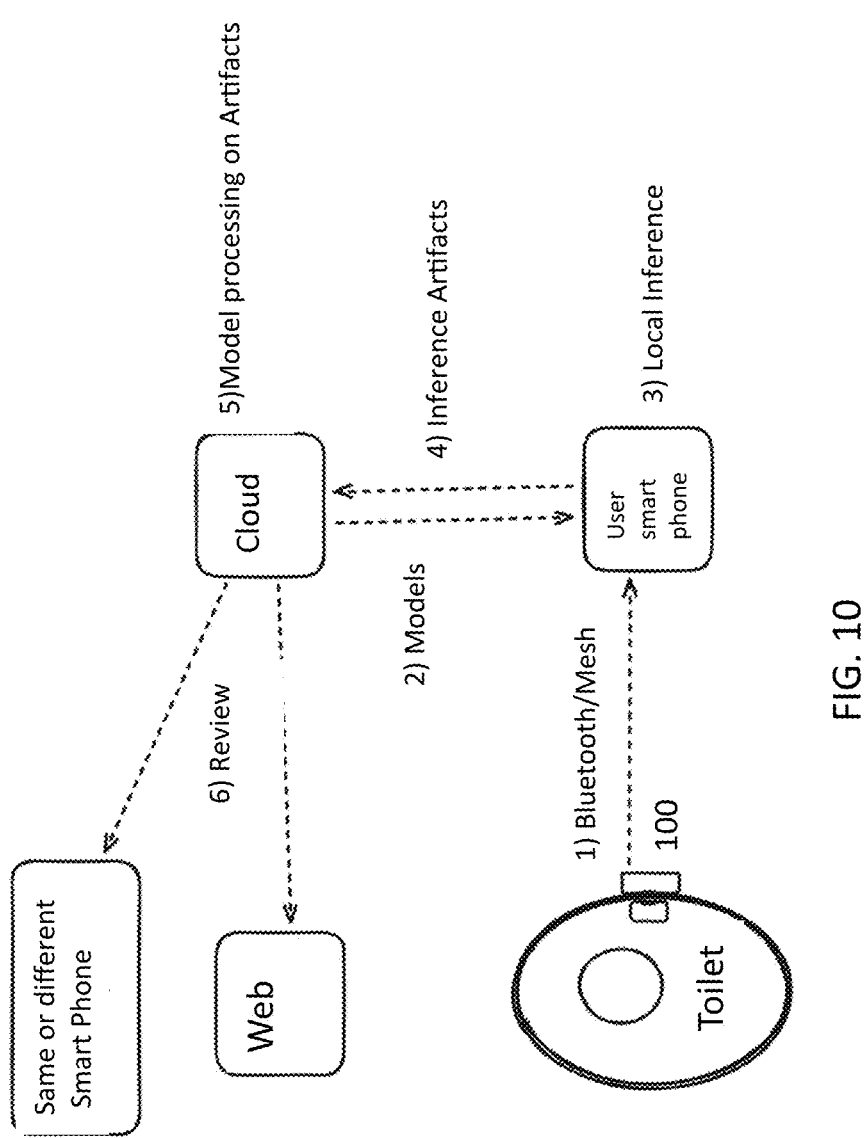
FIG. 10 generally illustrates a schematic of a system for monitoring and analysis of bodily emissions, in accordance with additional embodiments of the present disclosure.

Located on a top face of the front portion 40 is at least one sensor 90. Sensor 90 can be a TMOS type sensor or a passive infrared (PIR) sensor for detecting the presence and/or proximity of a user to the device. On the bottom of back portion 20, an image capture apparatus 26 is located. Adjacent and surrounding the image capture apparatus is a light emitting source 28. In the embodiment shown in FIG. 3, the light emitting source 28 is configured in a ring shape around the image capture apparatus 28. In other embodiments, the light emitting source can be located anywhere on back portion 20, as long as it is positioned so that it emits light within the internal portion and/or surfaces of a toilet bowl. As can be seen in FIG. 4A, the image capture apparatus 26 is configured to be at an angle and does not face straight down into a toilet bowl. The embodiment shown in FIG. 4A details the image capture apparatus 26 is positioned in a tilted angle, so as to face towards the central internal portion of a toilet, when the device is mounted on the side wall/rim of a toilet.

Illustrated in FIG. 4C if a front view of device 100, with front portion 40 shown more clearly. Front portion 40 has a central region 44, where various buttons and/or user inputs can be located (not shown for simplification). On a bottom surface of front portion 40, a charging port 80 is incorporated, for recharging the device as needed.

In one embodiment, the image capturing apparatus 26 is a multispectral or hyperspectral camera configured to capture images across multiple spectral bands. A multispectral camera has the capability to capture images beyond that in the visual light spectrum. In one embodiment, a multispectral camera has a spectral range between 420-870 nm. In a further embodiment, the image capturing apparatus can comprise a hyperspectral camera, which is capable of capturing images in a broader spectral range, including 400 to 2500 nm.

As noted above, the device 100 incorporates at least one sensor. In one embodiment, a sensor comprises a passive infrared (PIR) motion sensor for detecting when a user is in proximity of the device, thereby indicating to the device that a user will be using the toilet. The PIR sensor can be programmed to identify an infrared fingerprint unique to each specific programmed user of the device. In another embodiment, the device can incorporate one or more load or pressure sensors, which sense pressure placed upon the seat of the toilet, thereby indicating that a user is seated on the toilet. The load or pressure sensor can also be utilized for purposes of identifying the user seated on the toilet. This type of sensor can capture the weight of the user, and can thereby identify the user based on this weight data, particularly in instances when multiple users are programmed to use the device. The system's user recognition capabilities can be enhanced by incorporating data inputs from multiple sensors, such as PIR, video, audio, etc.

In a further embodiment, the device can incorporate an ambient light sensor, for detecting when a user has entered a bathroom and turned on the light. Similar to the PIR motion detection sensor, this allows the device to activate various components in preparation for the user being seated on the toilet.

As previously disclosed and shown in FIGS. 1-4C, the device 100 incorporates a light emitting source 28 is for illumination of the internal portion of the toilet, while a user is using the toilet, and for illumination of the contents of the bodily emissions for purposes of image capturing and data gathering during that use. In one embodiment, the light emitting source is at least one LED or an array of one or more LEDs, which emit light in the visible light, near ultraviolet, and near infrared spectra. The image capturing apparatus can obtain multiple images of a single session with varying lighting illumination that includes a variety of wavelengths along the electromagnetic spectrum including infrared, visible, and ultraviolet light. For example, images may be obtained while a blue light is emitted, or a red light, or a green light, or UV wavelengths, or infrared wavelengths, or a combination thereof. For example, illumination of blue light of a urine sample can cause certain bacteria or porphyrins to fluoresce. This in turn can aid in the detection of metabolites, infections and/or related substances that can be identified through fluorescence.

Further light emitting sources can also be incorporated, for purposes of sanitation and disinfection of the device and/or surrounding toilet surfaces. In one embodiment, the device incorporates a UV light source, which emits light in the ultraviolet region. The UV light source can be placed internally within the device and emit UV light to the surfaces of the device, from its internal location. In such embodiments, the device body is comprised of a transparent housing and the emission of UV light on the surfaces serves to disinfect and sanitize the surfaces of the device, including internal and external surfaces. In further embodiments, the UV light can be positioned so that it emits light externally from the device to the surrounding toilet surfaces, for disinfecting and sanitizing the surrounding surfaces within the interior of the toilet bowl or the contact surfaces of the toilet seat.

In certain embodiments, the device further comprises an audio capturing apparatus, such as at least one microphone or at least one microphone array. The microphone or microphone array has sound capture capability in the 20 Hz to 20,000 Hz frequency range. In some embodiments, the audio capturing apparatus is configured to detect uroflometry or sonouroflowmetry data related to a user's voiding of urine. The uroflometry or sonouroflowmetry data is analyzed to determine the flowrate, or duration of the user's urine voiding. In one embodiment, this data can be used to determine if a user has normal or abnormal urine flow, which is known to be associated with certain urologic disorders. In certain embodiments, captured images are used to analyze the color of urine and determine certain parameters related to the content of the urine. In certain embodiments, data is obtained that tracks the average color of the toilet water while mixing with urine is occurring as the urination proceeds. The rate of change of the color of the toilet water and urine color estimation can provide a baseline for flow rate estimations. Similarly, the duration of voiding and flow rate estimates can be used to provide a grounding volume estimate for the sonouroflowmetry, which can in turn provide highly accurate urine flow rate estimates.

The device can have an external power source, an internal power source, or a combination thereof. For example, in one embodiment the device incorporates a rechargeable battery, located internally within the device body's front portion 40. A battery monitor is also included to monitor battery life of the device. Battery health can be shown on indicator light on the device, displayed on the user interface (e.g. smartphone) or via LEDs illuminating the bowl of the toilet. The battery is configured to provide extended life to the device, including up to 6 months on a single charge. A lithium battery with at least 5000 mAh can be used. Also incorporated is a 5V USB C input for charging the battery. Alternatively, alkaline batteries can be utilized, which do not require recharging and can be replaced at end of charge. A battery management system can be included that utilizes an energy efficient design. This includes programming of adaptive power-saving modes for the device, during extended periods of time when the device will not need to be active and in use. The battery management system is configured to activate powering of various components of the device, when a specific sensor detects presence of a user (this includes the sensors previously discussed above). Said battery may be recharged with a contact-free power supply to provide electrical safety in a potentially wet environment.

The processor incorporated within the device gathers data from the image capturing apparatus and/or the various sensors and transmits data to an analysis system that includes artificial intelligence processing capability. The processor can be incorporated on a PCB. Preferably, the PCB includes wi-fi and Bluetooth® capabilities for receiving and transmitting data. In one embodiment a low-power MCU-based system on a chip (SoC) is used, which incorporates power management capabilities and wi-fi/Bluetooth® connectivity. One such example is the ESP32-S3 SoC, available from Espressif Systems. In certain embodiments, the analysis system is sealed in a water impermeable casing to prevent damage in a wet environment.

The data gathered from the various device components, including the image capturing apparatus, audio capturing apparatus, or the various sensors, is transmitted from the processor to an analysis system that incorporates artificial intelligence (AI) processing capability. In some embodiments, the AI based analysis system may include one or more machine learning models that are trained to perform any of the techniques disclosed herein. The one or more machine learning models may be generated by a training engine and may be implemented in computer instructions executable by one or more processing devices of the training engine and/or servers. To generate the one or more machine learning models, the training engine may train the one or more machine learning models.

The training engine may be a rackmount server, a router computer, a personal computer, a portable digital assistant, a smartphone, a laptop computer, a tablet computer, a netbook, a desktop computer, an Internet of Things (IoT) device, any other desired computing device, or any combination of the above. The training engine may be cloud-based or a real-time software platform, and it may include privacy software or protocols, and/or security software or protocols.

Using training data that includes training inputs and corresponding target outputs, the one or more machine learning models may refer to model artifacts created by the training engine. The training engine may find patterns in the training data wherein such patterns map the training input to the target output, and generate the machine learning models that capture these patterns. The one or more machine learning models may comprise, e.g., a single level of linear or non-linear operations (e.g., a support vector machine [SVM]) or the machine learning models may be a deep network, i.e., a machine learning model comprising multiple levels of non-linear operations. Examples of deep networks are neural networks including generative adversarial networks, multimodal large language models (LLMs), visual transformer models, convolutional neural networks, recurrent neural networks with one or more hidden layers, and fully connected neural networks (e.g., each neuron may transmit its output signal to the input of the remaining neurons, as well as to itself). For example, the machine learning model may include numerous layers and/or hidden layers that perform calculations (e.g., dot products) using various neurons.

In one embodiment, the one or more machine learning models may be trained by training input data that includes labeled images of stool, urine or a combination thereof. In another embodiment, machine learning models may be trained by training input data that includes processed images of stool, urine, or a combination thereof, said processing to include Fourier transforms of said images as a function of electromagnetic wavelengths. In an example, image data can be input that is labeled with respect to urine osmolality based from urine color. An ML model can then be trained to predict urine osmolality from color based analysis.

In a further embodiment, input data can include labeled segments of a session video with one or more labels that describe the action that is occurring in the video during that interval of time (e.g., active urine voiding, active fecal excretion, flushing, toilet paper present, blood present, and so on).

Additional training input data can include audio recordings of urine voiding, which are labeled and mapped to specific output targets, including for example urologic parameters, or urologic health indicators. In one example, audio recordings of urine simulant (colored water) can be utilized as inputs. An automatic system can be utilized that pumps colored water into a toilet bowl at different heights, different flow rate curves, different duration, and so on. Audio and image inputs are collected and labeled. The input labeled audio recordings and images may be mapped or correlated to specific parameters that are indicative of certain diseases, medical conditions, or other health related indications. The ML models are trained based on the combination of inputs, including visual and audio data.

In one embodiment, the ML models are trained on labeled image inputs that are indicative of the presence of blood in stool and/or urine. The labeled image inputs may include image data collected from images with blood simulant (e.g., animal blood or artificial blood) and stool simulant in a controlled environment. Image data can also include images from samples of blood in various quantities and in various configurations in a controlled environment. Examples include dripping blood into a toilet or embedded blood in a fecal-matter simulant. Input image data can also be synthetically generated. For example, data can include computer-generated images of stool and urine with varying degrees of blood presence. This can augment the dataset without relying solely on real samples. Image input can also be obtained on an anonymous basis from healthcare providers or clinical research facilities and labelled according to various medical diagnoses for stool and urine samples. Once the AI based analysis system makes a determination that the current data transmitted from the user indicates presence of blood, the AI based model can perform a control action that will cause the device or the user interface/visual display to alert the user to this determined parameter. If repeated instances of blood detection are determined by the AI based analysis system, then the system may generate recommendations to the user to seek out a healthcare professional. The AI based analysis system can also generate informational material for the user that provides a differential diagnosis of known causes of blood in the stool. The AI based analysis system can also generate informational material for the user that provides a differential diagnosis of known causes of blood in the stool. In repeated instances of blood detection, the AI based analysis system may be trained to recognize patterns of blood that matches with known causes aiding in the diagnosis.

In a further embodiment, the ML models are trained on inputs of images that are labeled and mapped to specific Bristol Stool Scale classifications, indicating the condition of the user's stool (e.g., ranging from hard to loose stool). Based on mapping the user's image data, the AI based analysis system can generate recommendations to the user, including ways to improve stool consistency to normal levels, and such recommendation is transmitted and communicated through the user's interface.

In further embodiments, the ML models are trained on inputs of images of stool samples that are correlated with fecal calprotectin levels. For example, stool images can be collected from participants, which are submitting these fecal samples for fecal calprotectin testing. Calprotectin is a biomarker indicate of colonic mucosal inflammation. The collected images are labeled with the fecal calprotectin scores obtained from the testing. The labeled dataset is used as inputs in the ML model for purposes of estimating fecal calprotectin scores from input stool images. This results in a non-invasive means of monitoring gut health and assessing potential colonic mucosal inflammation.

In a further embodiment, the AI based analysis system can further include input from user-submitted third-party health data, which the user self-reports based on various medical historical events or testing. For example, user-submitted health data from third-party tests can be collected and input, including but not limited to fecal calprotectin levels, blood tests, and urinary chemical paper strip tests for specific gravity. These test results into the systems database to enhance the accuracy and predictive capabilities of the AI analysis system. User submitted data can be utilizes to develop personalized health models for individual users, tailoring health recommendations and insights to their specific biomarker profiles.

In additional embodiments, the AI based analysis system can generate recommendations based on what is detected in the urine and/or stool. For example, if the urine is a certain color (e.g., dark yellow), the AI based analysis system may determine the user is dehydrated and may generate a recommendation that the user might increase consumption of liquids. In other instances, the urine color may indicate the presence of bilirubin that flags the possibility of gallstones blocking ducts carrying bile out of the liver or other problems in bilirubin processing. Further, dark brown urine may be a sign of rhabdomyolysis, a serious condition caused by muscle tissue death, black urine may be indicative of alkaptonuria caused by disordered breakdown of amino acids, hematuria—blood in the urine—may indicate urinary tract infection, prostate infection, kidney stones, or cancer. Green urine or cloudy urine may indicate a urinary tract infection. Chyluria, a condition when the digestive substance chyle is in the urine, may indicate a lymphatic parasitic infection. Foamy urine may indicate diabetes or kidney disease.

In one example, the determined parameter can include the presence of undigested or partially digested foods and insoluble fibers in stool. Other parameters can include low urine volume, or color parameters of urine, suggesting health-related information such as the user's hydration levels. Additional examples of determined parameters include timing aspects of bowel movements that can be logged and analyzed, to provide the user information on the frequency of bowel movements, and track normal versus abnormal activity for that user. Parameters linked to time can include stool color, during of sessions, active versus passive time, distinct number of stool pieces for a given session, number of stool discharge events and their spacing in time. Historical activity can be tracked and analyzed, to alert the user when changes have happened that are abnormal based on that user's history. Historical data may be used to specify an individual user's baselines and analyze variations in that user's health parameters, enabling personalized health insights and allowing the device to flag deviations from both a user's baseline as well as from a generally accepted healthy range for a given parameter (i.e. Bristol Stool Scale, urine max flow rate, frequency of urination or excretion). The health related information can also include time-based trends and patterns from repeated measurement of the determined parameters, such trends and patterns that can be pathognomonic for diagnosis or exclusion of a disease such as regional ileitis. These trends and patterns can also provide input layers of neural networks to determine disease status, for example, highly inflamed or quiescent ulcerative colitis. Once the diagnosis of a disease has been made, a disease status (herein, "disease state") can be determined. For example, a patient with ulcerative colitis may be assigned the state of "active with active bleeding, ulceration, diarrheal content, and 47% probability of microbiome disorder, assigned 887 on a 1,000 point scale of disease state." This disease state might be daily measured over a week and the trend might be flat, meaning the initially assigned activity level of 887 might demonstrate no significant trend. Then, once disease state and trend are established, a single intervention variable can be determined. This intervention might be an increase in dietary food fiber, daily supplementation with a specific probiotic (e.g., *lactobacillus*), decrease in rapidly absorbed sugar, or an increase in anti-inflammatory medication, etc. After the intervention is initiated, the daily measurements are almost certain to indicate a positive trend (e.g., disease state of less than 887 or a negative trend (e.g., disease state trending consistently greater than 887). Trend measurement from an at-home allows a suffering patient to accurately assess the therapeutic benefit of serial interventions and navigate from high risk and poorly controlled disease states to dramatically improved states of existence. Note, this navigation capability is not the result of a single point measurement and disease state assessment but rather it derives from the ability of the device to serially measure disease state, store that information, and assess the trend of said disease status as a function of serial therapeutic interventions.

In one embodiment, the AI based analysis system analyzes and communicates to the user nutrition related data. For example, images taken with the image capturing apparatus of the device can be used by the AI based analysis system to determine the presence of certain insoluble fibers, that a user would have logged in as a consumed meal, through a user interface (i.e. an application on a mobile phone or personal computing device). Once a user logs in a specific meal and/or consumed ingredients through the user interface, the AI based analysis system can determine the user's digestive transit time of those ingredients (i.e. insoluble fibers), through image data. The digestive transit time can be utilized to determine if specific meals or ingredients are problematic for healthy bowel movements of the user. If a user logs in a specific meal multiple times, and a certain bowel movement characteristics are captured, then the AI based analysis system may make a determination that a particular meal or ingredient causes unhealthy digestive bowl activity for the user (such as loose stool, or constipation). This information is then communicated to the user through the visual display of the user interface (e.g., the mobile phone application). In this way, certain problematic foods, meals or ingredients can be flagged by the AI based analysis too and reported to the user, based on repeated abnormal stool activity related to that food or meal.

The logging of foods, ingredients or meals from the user's end can be achieved by capturing an image of the food or meal the user is consuming, through the camera of their phone and uploading it to the user interface (i.e. the app). The AI based analysis system can also be trained and utilized to recognize images of food and itemize specific ingredients within that image. The user can confirm or modify the ingredients determined by the AI system, to more accurately log the consumed food. Alternatively, or additionally the food logging from the user can be manually input through selection of a series of ingredients, foods or meals that are pre-programmed and selectable through the user interface.

The device and systems disclosed herein are intended to seamlessly incorporate into a user's daily routine, and be passive components that the user does not have to actively engage. For example, passive features of the device can include the incorporation of a Bluetooth received signal strength indicator (RSSI) that can be configured to attribute a session to a specific user based on which mobile device is closest to the device at the time the session is recorded. The signal strength would to surpass a threshold so that sessions are not mistakenly attributed to a user in proximity to the device, but not actually using the toilet. The load cell sensors incorporated on the device also contribute to the passivity of the device. Users can be identified based on specific loads identified from the sensors. For example, if no load is identified but a urination session begins, this may indicate to the device that a male subject from the programmable users is the current user. Audio recordings can also be configured to similarly identify users based on their footsteps and/or gait. The various sensing sources incorporated in the device attribute to a high degree of accuracy in user identification, to accurately attribute a session to the correct user, without the user having to actively input or actively log that he/she is using the toilet. A training or calibration process and time period may be utilized, wherein the user self identifies by using a record button on the user interface, or by having their mobile device with them during sessions for Bluetooth RSSI detection.

Also disclosed is a computer-implemented system, for monitoring and analysis of bodily emissions emitted from a user. The computer-implemented system comprises a device as described in all prior embodiments, a processor configured to receive data from one or more components of the device and transmit said data to an artificial intelligence based analysis system. The artificial intelligence based analysis system is configured to perform an analysis of the transmitted data, and determine at least one parameter from the analysis. The computer-implemented system further incorporates a user interface that communicates to the user health-related information based on the determined at least one parameter from the artificial intelligence based analysis system.

FIGS. 6-10 depict various embodiments of how components of the system for monitoring and analysis of bodily emissions are connected and or configured to communicate or store data. In the embodiment shown in FIG. 6, raw data from the device can be collected and transmitted to a cloud based network where it can be processed and stored. The AI based analysis system performs analysis of the data and presents target outputs to the user on a user interface (smart phone) or to any accessible web based platform.

For purposes of brevity, it is noted that all features of the device, processor, user interface, and AI based analysis system, detailed in all prior embodiments are incorporated herein with respect to the disclosed computer-implemented system, and need not be repeated.

The disclosure also pertains to methods for monitoring and analysis of bodily emissions emitted from a user. The methods may be implemented in computer instructions stored on one or more memory devices and executed by one or more processing devices. As can be seen in FIG. 11, in one embodiment, a method comprises:

at block 1101, providing a device for monitoring and analyzing bodily emissions, wherein said device is mounted on a toilet utilized by the user;

at block 1102, gathering data from the device and transmitting said data to an artificial intelligence based analysis system, wherein the artificial intelligence based analysis system is configured to, at block 1103, perform an analysis of the transmitted data and determine at least one parameter from the analysis; and at block 1104, communicating to the user health-related information based on the determined at least one parameter from the artificial intelligence based analysis system.

In other embodiments, methods for monitoring and analyzing a user's nutritional information are provided. In one embodiment, a method comprises:

providing a device for monitoring and analyzing bodily emissions, wherein said device is mounted on a toilet utilized by the user;

gathering data from the device and transmitting said data to an artificial intelligence based analysis system, wherein the artificial intelligence based analysis system is configured to perform an analysis of the transmitted data and determine at least one parameter from the analysis; and communicating to the user nutrition-related information based on the determined at least one parameter from the artificial intelligence based analysis system.

An additional embodiment incorporates one or more secondary devices that are configured to connect via WiFi or Bluetooth to the primary device disclosed in the above embodiments for monitoring and analyzing bodily emissions. These secondary devices would also be configured to be mounted on the toilet similar to the primary device.

In one embodiment, a secondary device comprises a load sensor for capturing weight distribution data of a user seated on the toilet. In this embodiment, the load sensors are therefore not incorporated on the primary device, as in prior described embodiments, but are incorporated as secondary devices, also mountable on the toilet, and configured to communicate with the primary device. The load sensor transmits the weight distribution data to the primary device. This additional data improves the accuracy of the Al-based prediction of the user's weight. The weight distribution data from multiple load sensors also aids in identification of the specific user.

Another secondary device embodiment utilizes a depth camera device pointed outwards toward the user's feet to provide information regarding the user's stance that can be transmitted to the primary device to aid in the identification of the specific user.

Another secondary device embodiment is a floor mat (not mounted on the toilet) placed in front of the toilet to capture the standing weight of the user to aid in the identification of the specific user using the toilet and in the Al-based prediction of the user's weight.

An additional embodiment comprises a secondary device that incorporates a software-controlled reagent dispenser. The primary device signals the reagent dispenser to release one or more colorimetric reagents upon detection of urine or feces. The reagents chemically react upon contact and cause color change or fluorescence proportional to the concentration of certain chemicals. This provides additional analytical sample data for the artificial intelligence system regarding the chemical composition of the excreted urine or stool. Various reagents can be utilized for example:

Leukocyte esterase reagent to indicate infection or inflammation in urine via purple color change Guaiac solution to indicate blood in stool via blue color change pH indicator reagents to denote acidity levels in urine or stool via color hue changes In another embodiment, the reagent dispenser device monitors volume of remaining reagents and communicates this to the primary device to prompt the user when refills are needed.

Another secondary device embodiment utilizes a camera device to provide stereoscopic imaging when used in conjunction with the primary device's camera. The dual camera views enable 3D reconstruction of stool samples to estimate volume or improve image training data for the artificial intelligence system.

An additional embodiment involves a laser-based spectrography module for enhancing the analytical capabilities of our health monitoring toilet system. This module features a diode laser, a spectrometer, and a CCD or CMOS detector arranged in a ring around the laser. The diode laser operates between 700 nm to 900 nm wavelengths, chosen for their effectiveness in biological sample analysis by minimizing fluorescence interference and maximizing tissue penetration. The laser's power can be adjusted from 50 mW to 500 mW, with pulse durations ranging from nanoseconds to microseconds, allowing for flexible Raman signal acquisition across different sample types and concentrations. The spectrometer, coupled with a CCD or CMOS detector, captures backscattered light with high precision across a spectral range of 200 nm to 1100 nm. This enables the identification and quantification of various chemical compounds in urine and feces. When activated by the primary device upon waste detection, the module uses the diode laser to induce a Raman scatter in the sample. The spectrometer analyzes this scatter to identify and quantify biomarkers like glucose, based on their spectral fingerprints. This chemical profile is wirelessly transmitted to the primary device.

Another secondary device embodiment incorporates a software-controlled air freshener that is signaled by the primary device to dispense a mist of odor blocking oils into the toilet water when the primary device detects an applicable event such as when the user is engaged in defecation.

Further secondary devices can be configured with any combination of the disclosed sensors to provide supplemental sensor data to the primary sensing device. Notably, it is also contemplated within the scope of this disclosure that certain embodiments of these secondary devices, or their functional components, could be integrated directly into the primary device. This integration aims to enhance the primary device's sensing capabilities by incorporating the diverse functionalities of secondary devices, thereby offering a more comprehensive and versatile sensing solution.

An additional embodiment (not mounted on the toilet) provides flushable wet wipes soaked in colorimetric reagents analogous to those previously described. Upon contact with urine or stool, the colorimetric reagents cause color changes indicative of certain chemicals/conditions, providing user test data.

Figure 12:
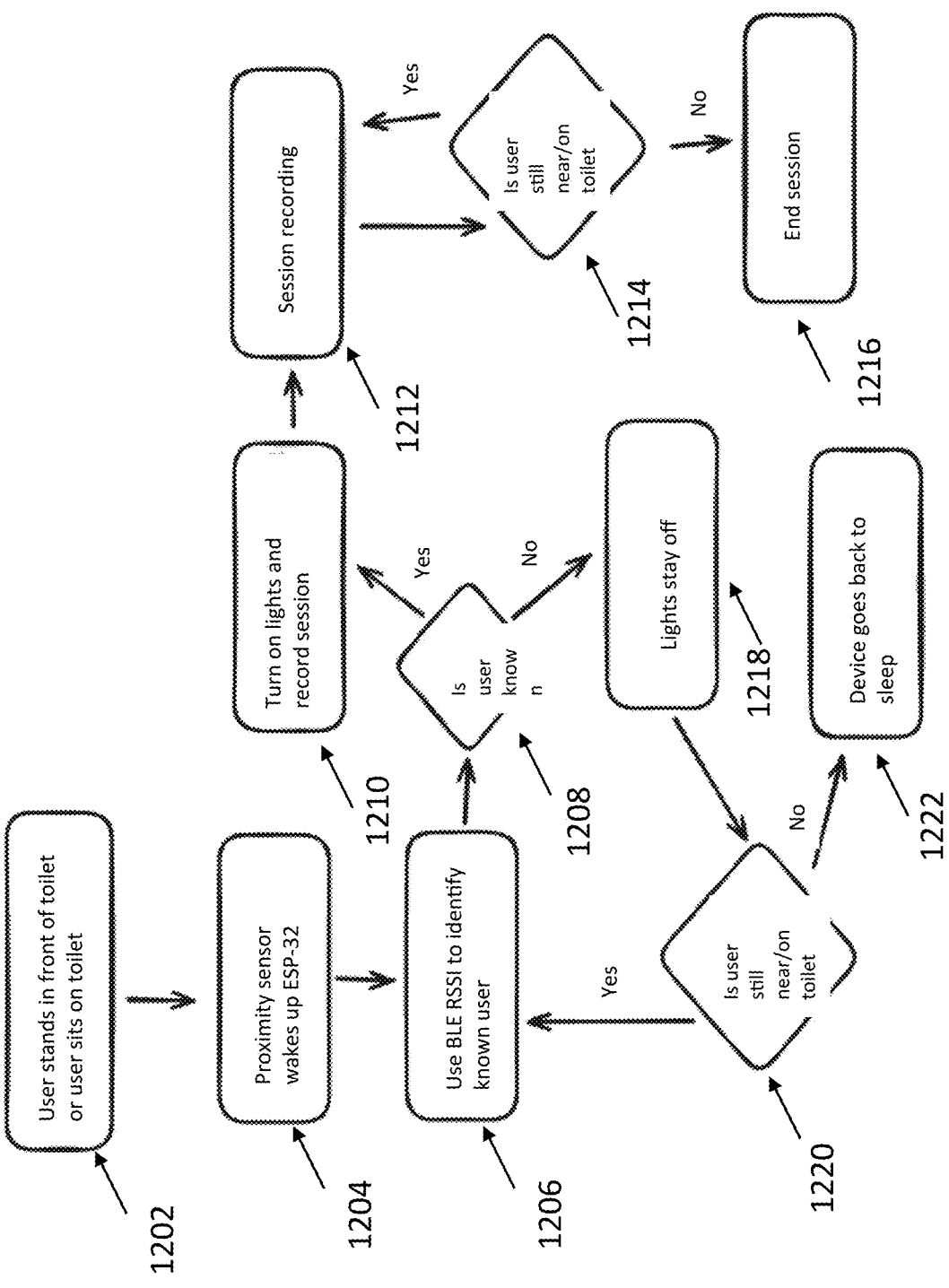
FIG. 12 generally illustrates a method related to determining whether a user is known and recording a session, in accordance with embodiments of the present disclosure.

FIG. 12 generally illustrates a method 1200 related to determining whether a user is known and recording a session, in accordance with embodiments of the present disclosure. The method 1200 may be performed by processing logic that may include hardware (circuitry, dedicated logic, etc.), software, or a combination of both. The method 1200 and/or each of their individual functions, subroutines, or operations may be performed by one or more processing devices of one or more computing devices implementing the method 1200. The method 1200 may be implemented as computer instructions stored on a memory device and executable by the one or more processing devices. In certain implementations, the method 1200 may be performed by a single processing thread. Alternatively, the method 1200 may be performed by two or more processing threads, each thread implementing one or more individual functions, routines, subroutines, or operations of the methods. In some embodiments, one or more accelerators may be used to increase the performance of a processing device by offloading various functions, routines, subroutines, or operations from the processing device.

For simplicity of explanation, the method 1200 is depicted and described as a series of operations. However, operations in accordance with this disclosure can occur in various orders or concurrently, and with other operations not presented and described herein. For example, the operations depicted in the method 1200 may occur in combination with any other operation of any other method disclosed herein. Furthermore, not all illustrated operations may be required to implement the method 1200 in accordance with the disclosed subject matter. In addition, those skilled in the art will understand and appreciate that the method 1200 could alternatively be represented as a series of interrelated states via a state diagram or events.

In some embodiments, one or more machine learning models may be generated and trained by an artificial intelligence engine and/or a training engine to perform one or more of the operations of the methods described herein. For example, to perform the one or more operations, the processing device may execute the one or more machine learning models. In some embodiments, the one or more machine learning models may be iteratively retrained to select different features capable of enabling optimization of output. The features that may be modified may include a number of nodes included in each layer of the machine learning models, an objective function executed at each node, a number of layers, various weights associated with outputs of each node, and the like.

At block 1202, a user stands in front of a toilet or sits on a toilet.

At block 1204, a proximity sensor wakes up one or more processing devices (ESP-32) by detecting the presence of the user standing in front of the toilet or sitting on the toilet.

At block 1206, one or more processing devices may use BLE received signal strength indicator (RSSI) to identify if the user is known by the system. For example, a mobile device carried by the user may emit a signal via BLE and the one or more processing devices of the device may determine whether the signal emitted is associated with a user of the system. In some embodiments, a camera may use facial recognition to analyze the user's face and determine if the user is known by the system.

At block 1208, one or more processing devices may determine if the user is known by the system. If yes, at block 1210, one or more processing devices may turn on illumination lights of the device to illuminate at least part of the toilet. Further, at block 1210, one or more processing devices may begin recording a session while the user uses the toilet. At block 1212, one or more processing devices of the device may record the session and, at block 1214, the one or more processing device may determine if the user is still near or on the toilet. If yes, the one or more processing devices continue to record the session while the user uses the toilet. If no, the one or more processing devices ends the session. The one or more processing devices may store the data associated with the session for the user, and/or may process the data using artificial intelligence.

If the user is not known by the system at block 1208, the one or more processing devices may keep the illuminating lights in an off state at block 1218. The one or more processing devices may determine whether the unknown user is still near or on the toilet at block 1220. If no, the one or more processing devices may cause the device to enter a sleep mode at block 1222. If yes, the one or more processing devices may continue to use BLE RSSI to identify if the user/mobile device is known by the system. Further, the remaining steps 1208-1220 may be repeated as applicable.

Figure 13:
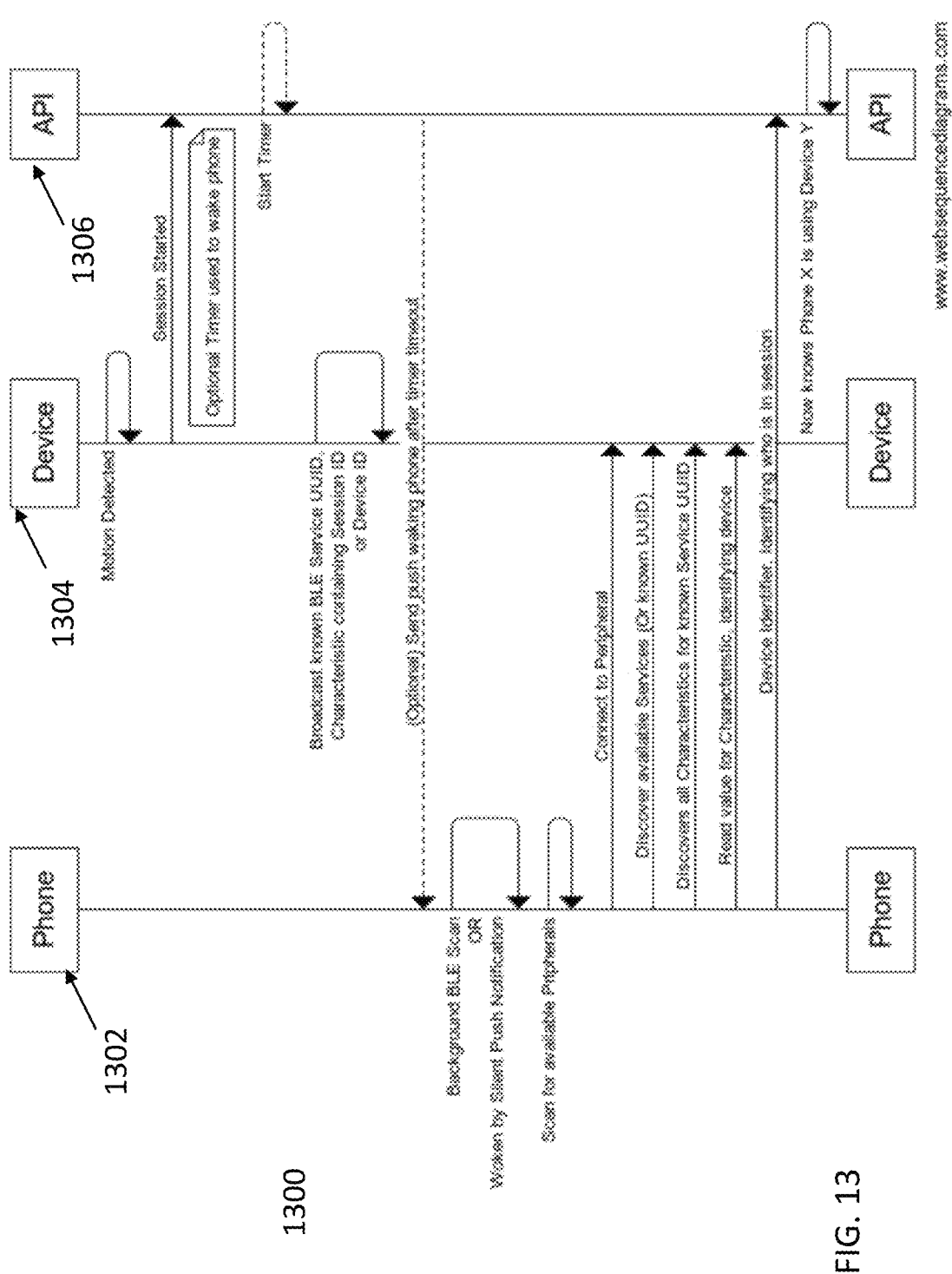
FIG. 13 generally illustrates a sequence diagram for initiating a session between a phone and a device, in accordance with embodiments of the present disclosure.
Figures 14A, 14B, 14C:
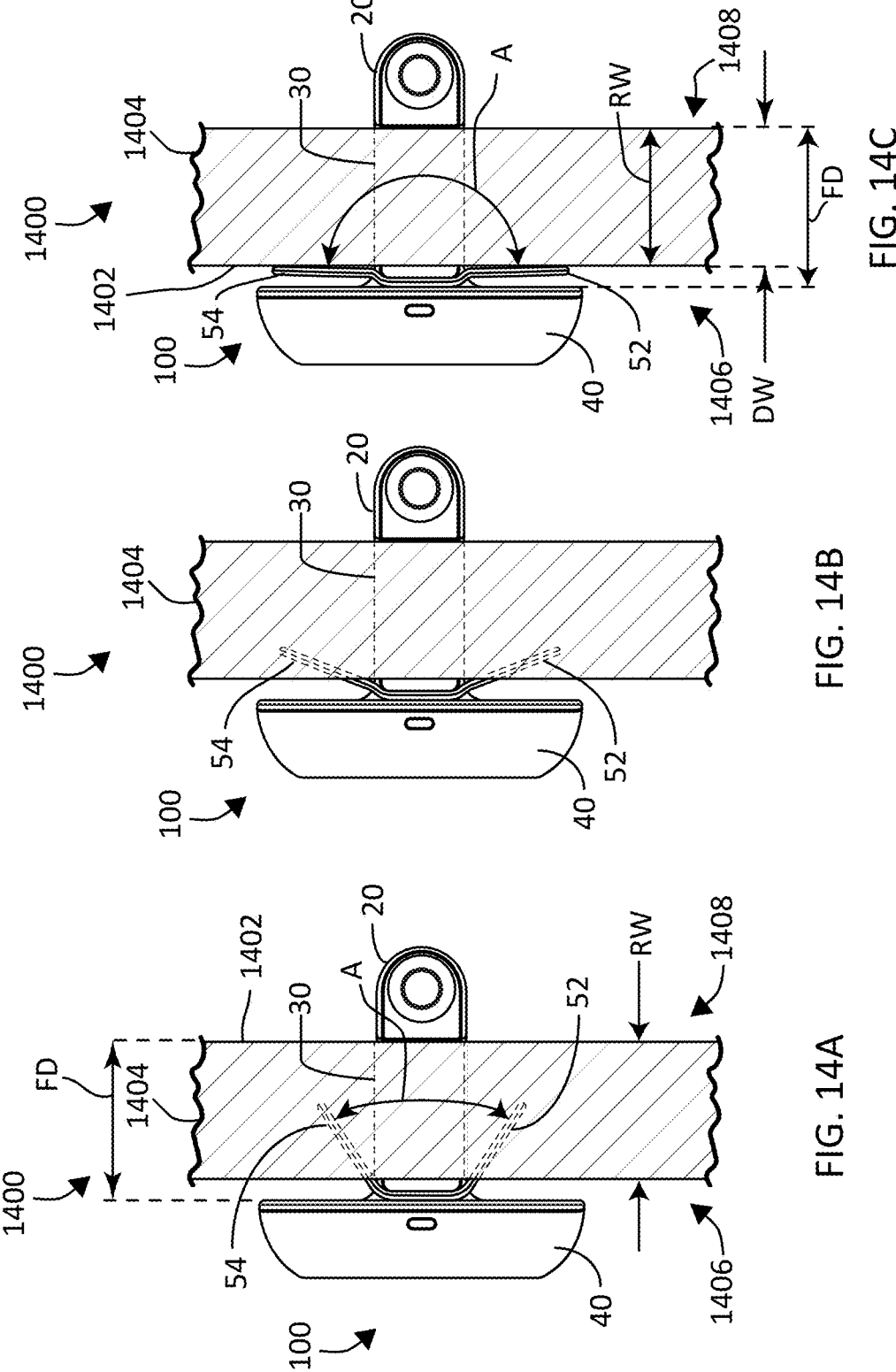
FIGS. 14A-14C are sequential bottom views of the device of FIG. 1 being mounted to a toilet rim, which is shown in sectional view.
Figure 14D:
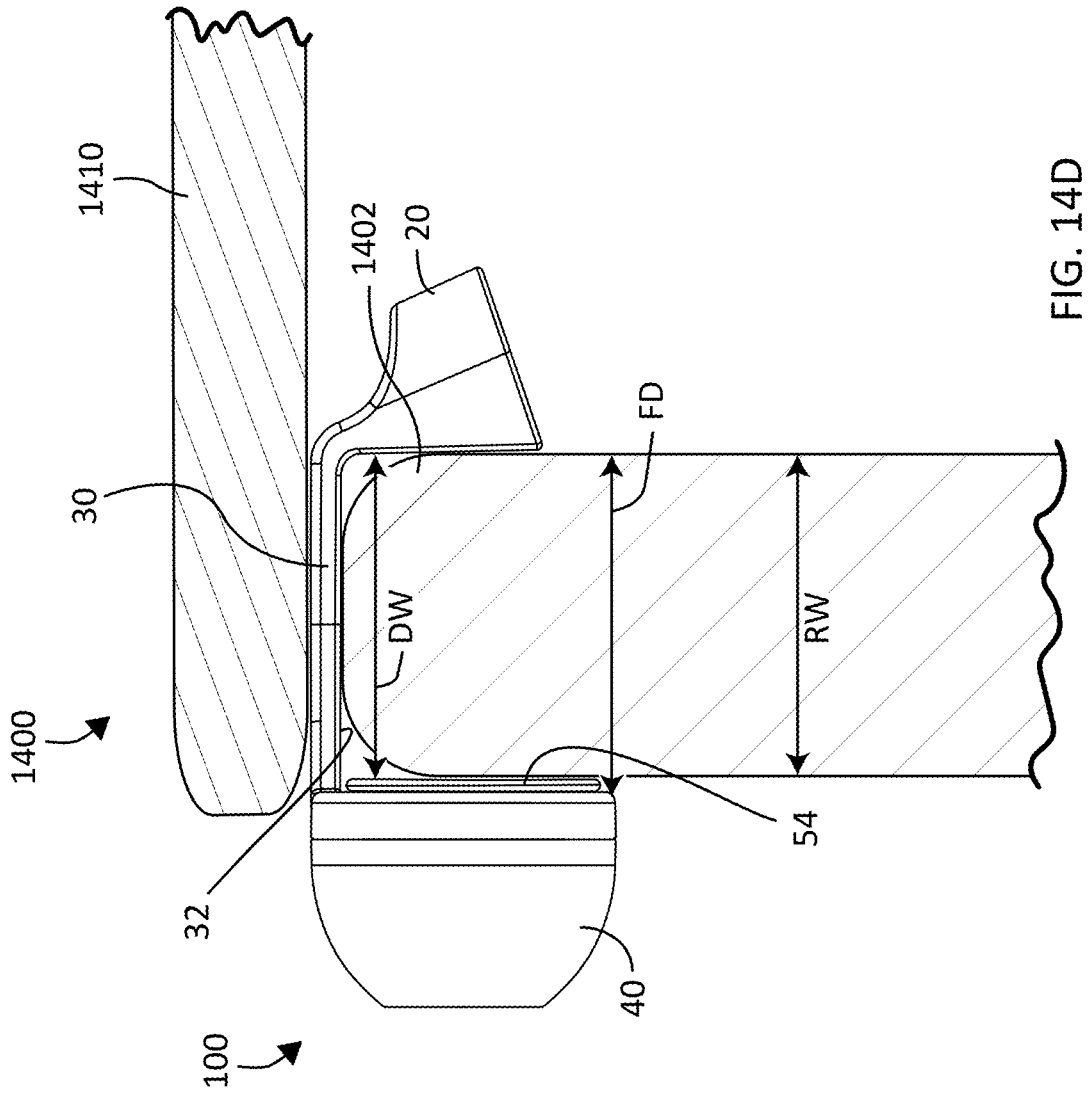
FIG. 14D is a side view of the device and toilet rim of FIG. 14C.
Figure 15:
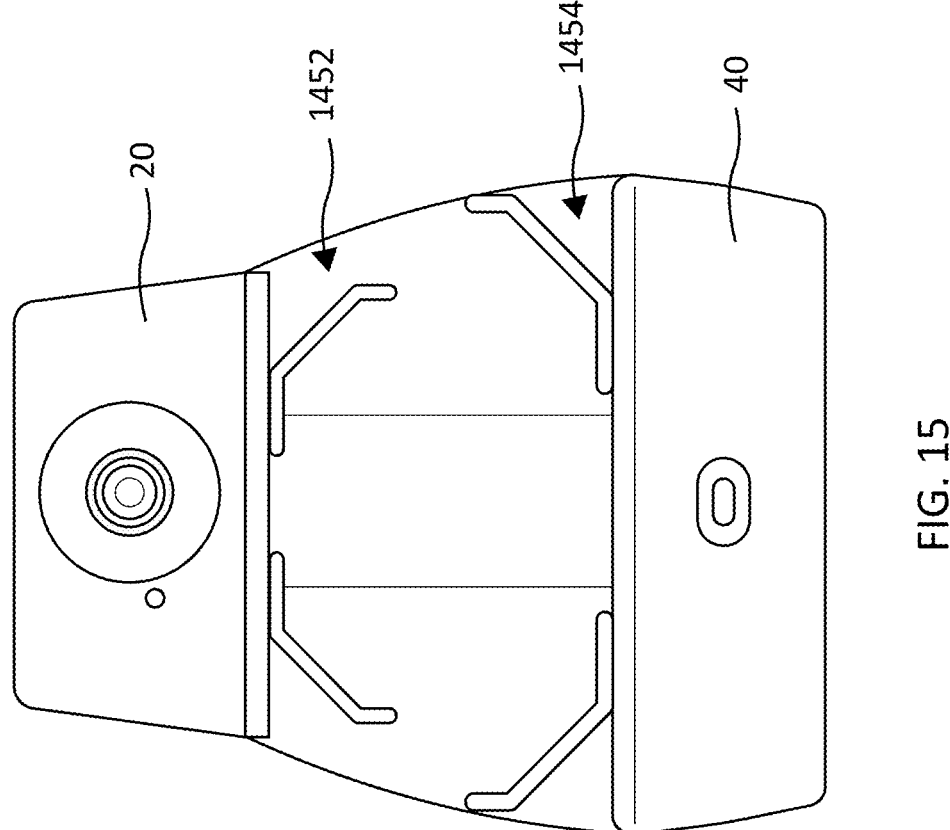
FIG. 15 is a bottom view of an alternate embodiment of a device.

FIG. 13 generally illustrates a sequence diagram 1300 for initiating a session between a phone 1302 (e.g., mobile device) and a device 1304, in accordance with embodiments of the present disclosure. Further, the sequence diagram may include an application programming interface (API) 1306.

The sequence may be initiated by the device 1304 detecting motion using a proximity/motion sensor, for example. When motion is detected by the device 1304, the device 1304 may transmit a message to the API 1306 that starts a session. In some embodiments, the device 1304 an optional time may be used to wakeup the mobile device. The device 1304 may transmit a message to the API 1306 to start the timer. In some embodiments, the timer may be set for a configurable amount of time (e.g., seconds, minutes, hours, etc.).

The sequence may continue by the device 1304 broadcast known BLE service universal unique identifier (UUID), characteristic containing session ID and/or device ID. In some embodiments, the sequence may include the API transmitting an optional push notification that wakes up the phone 1302 after the timer expires.

The sequence may continue by the phone 1302 performing a background BLE scan or is woken up by a silent push notification from the API 1306. The phone 1302 may scan for available peripherals, and if the phone 1302 detects the BLE broadcasted from the device 1304, the phone 1302 may connect to the peripheral (device 1304). The phone 1302 may discover available services (or the known UUID). The phone 1302 may discover all characteristics for known service UUID. The phone 1302 may read value for characteristics, identifying the device 1304. Further, the phone 1302 may transmit a device identifier and information identifying a user that is participating in a session to the API 1306.

The sequence may continue by the API 1306 determining that the mobile phone 1302 is using the device 1304. Further, the API may record any data pertaining to the session for the user received from the phone 1302 and/or the device 1304.

Referring now to FIGS. 1-3 and 14A-14D, embodiments of the device 100 may be mounted to the rim 1402 of a bowl 1404 of a toilet 1400. The front body 40 can be located on an exterior 1406 of the bowl 1404, and the rear body 20 can be located in an interior 1408 of the bowl 1404. The bridge 30 can couple the front body 40 to the rear body 20 at a fixed distance FD (FIG. 14A) therebetween such that the device 100, when installed, can straddle the rim 1402.

Embodiments of the attachment arms 52, 54 may comprise one or more flexible member(s). The flexible member may be located between the front body 40 and the rear body 20. The flexible member can adaptably accommodate a width RW of the rim 1402 that is less than the fixed distance FD to define a device width DW (FIG. 14C), to removably secure and retain the device 100 on the rim 1402. Thus, when installed, the device width DW can be equal to the rim width RW as the device 100 grips the rim 1404. Examples of the fixed distance FD can be not adjustable, and the device width DW can be adjustable to accommodate a range of rim widths RW from about 1 inch to about 2.5 inches. In some versions, the device 100 can clamp and be retained on the rim 1402 without fasteners.

Examples of the bridge 30 can include an underside flat 32 (FIGS. 1 and 14D) that, when the device 100 is installed, can lay flat on top of the rim 1402. In addition, a backside 42 of the front body 40 and a front side 22 of the rear body 20 can be parallel to each other. In one embodiment, the bridge 30 can be perpendicular to the backside 42 and the front side 22.

Again referring to FIG. 14D, a portion of the device 100 can be located between the rim 1402 and a seat 1410 of the toilet 1400. In one example, the device 100 is configured to not make contact with the seat 1410.

As shown in FIG. 1, the flexible member or attachment arms 52, 54 can include a contoured edge 56 that allows the flexible member to slide and move away from the rim 1402 as the device 100 is pushed down onto the rim 1402. In some examples, the contoured edge 56 is semi-circular and provides a lead in or sloped entrance when the device 100 is installed on the rim 1402. In one version, the flexible member is bonded to and extends from the backside 42 of the front body 40, but it also can be integrally formed as a single monolithic component.

Embodiments of the flexible member can comprise a cantilevered fin (again see attachment arms 52, 54) that is pliable and can flex (see FIGS. 14A-14D) and hingedly mounted to the front body 40. Versions of the flexible member can flexibly interface with the outer side of the bowl 1404. In another example, the flexible member can comprise a cantilevered fin that is rigid and hingedly mounted to the front body 40. As shown in FIG. 1, the flexible member can include two cantilevered fins that are diagonal to the front body 40 and extend in different directions. An angle A can be defined between the two cantilevered fins and, in an undeformed configuration (FIG. 14A), the angle A can be less than 90 degrees. In a deformed configuration (FIG. 14C), the angle A can be greater than 90 degrees.

Figures 16A, 16B, 16C:
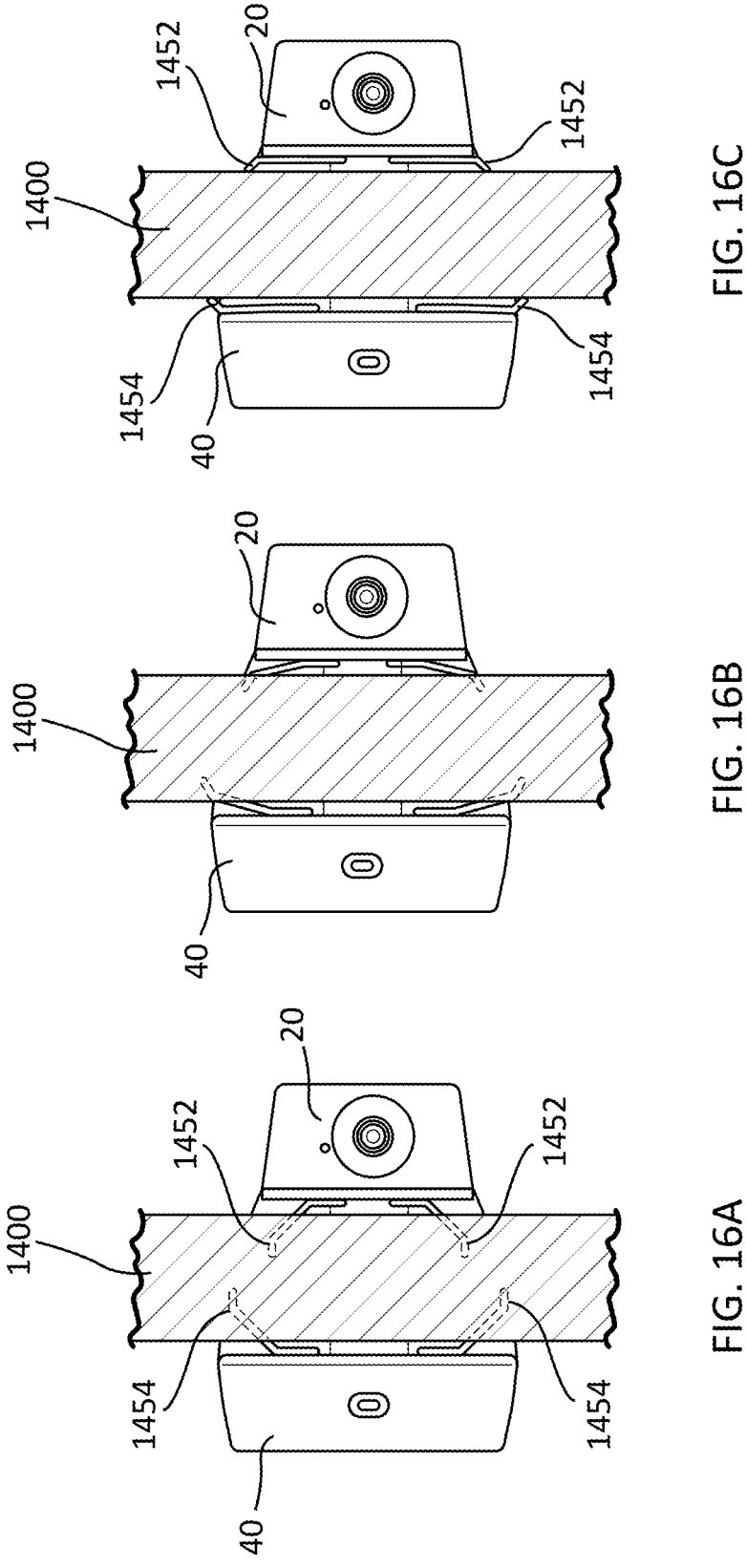
FIGS. 16A-16C are sequential side views of the device of FIG. 15 being mounted to a toilet rim.
Figure 17:
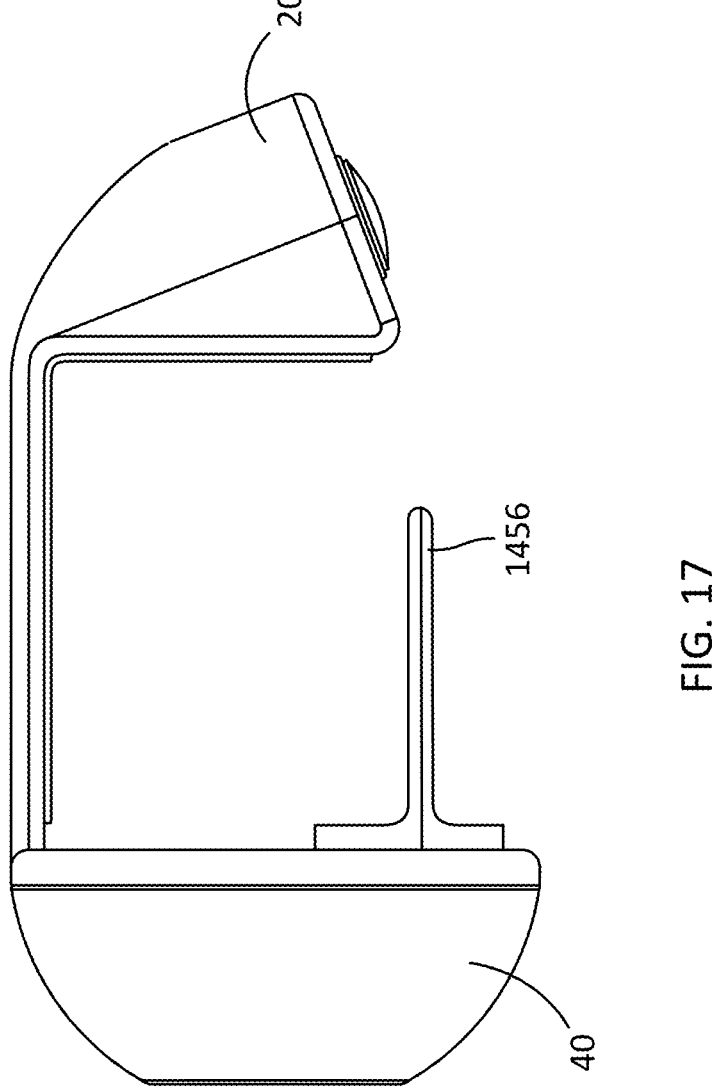
FIG. 17 is a side view of another alternate embodiment of a device.
Figures 18A, 18B, 18C:
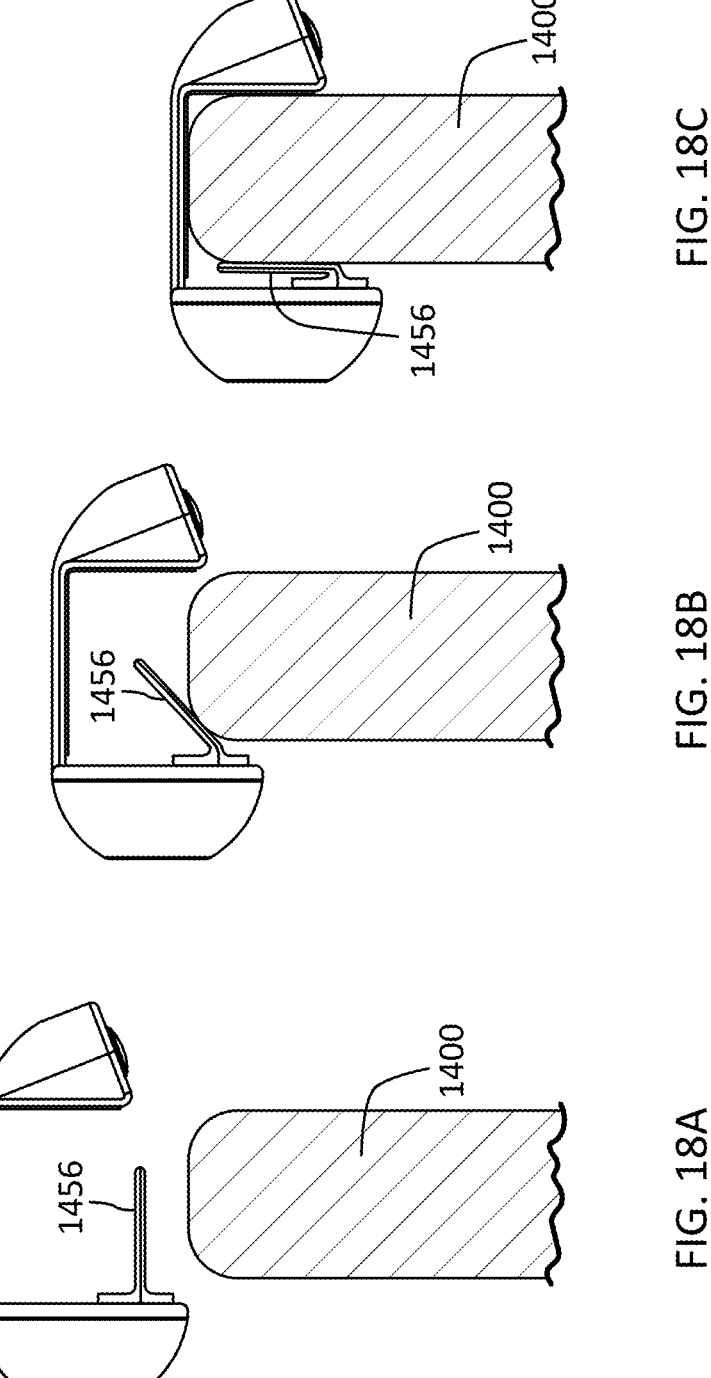
FIGS. 18A-18C are sequential side views of the device of FIG. 17 being mounted to a toilet rim.

As shown in FIGS. 15 and 16A-16C, the flexible member can comprise two pairs of cantilevered fins 1452, 1454 that are diagonal to the front body 40 and the rear body 20, respectively, and the cantilevered fins 1452, 1454 can extend in different directions. FIGS. 16A-16C show the cantilevered fins 1452, 1454 in progressive states of deflection as the device is installed on a toilet 1400.

Alternatively, the flexible member can comprise only one cantilevered fin 1456 (FIGS. 17 and 18A-18C) that extends from one of the front and rear bodies 40, 20. The only one cantilevered fin 1456 can be substantially horizontal and substantially perpendicular to said one of the front and rear bodies 40, 20.

Figure 19A:
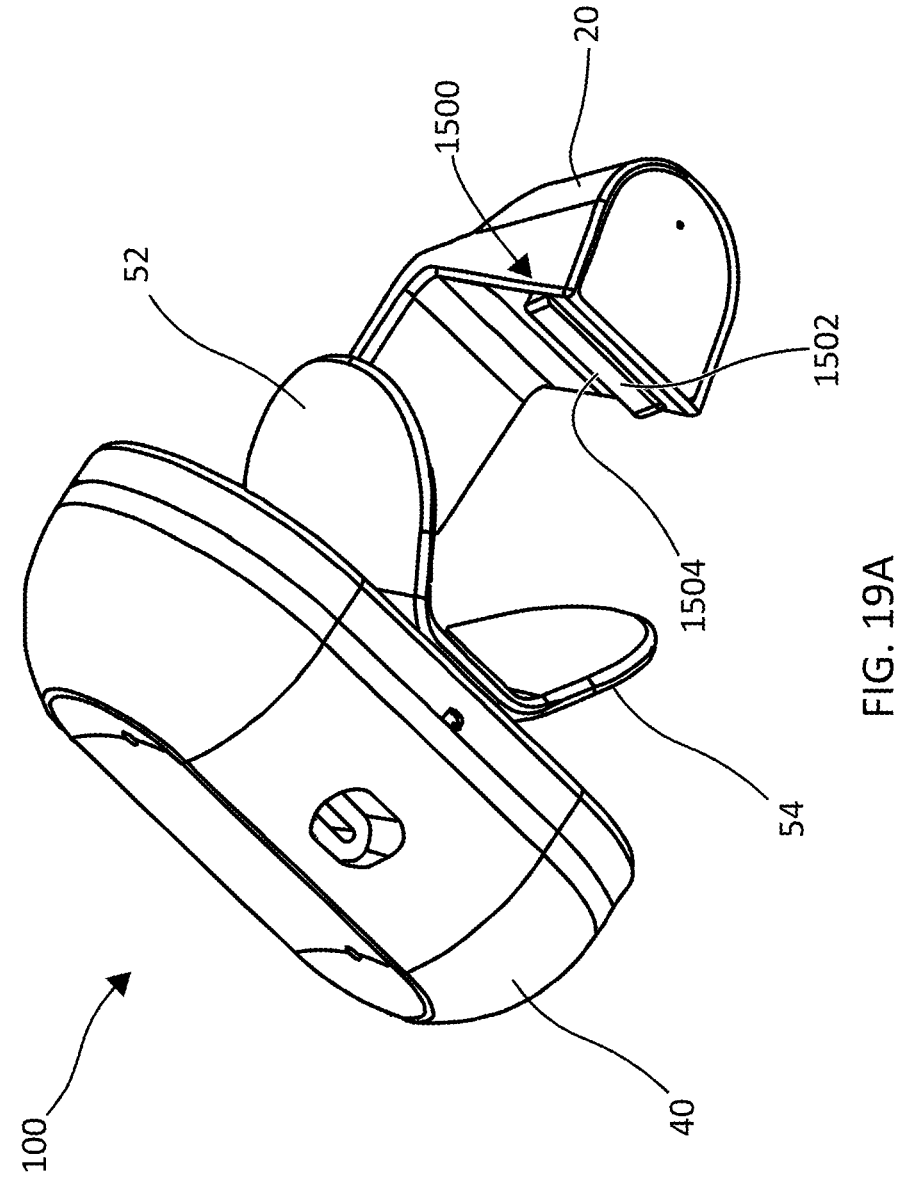
FIG. 19A is an isometric view of another embodiment of the device.
Figures 19B, 19C, 19D:
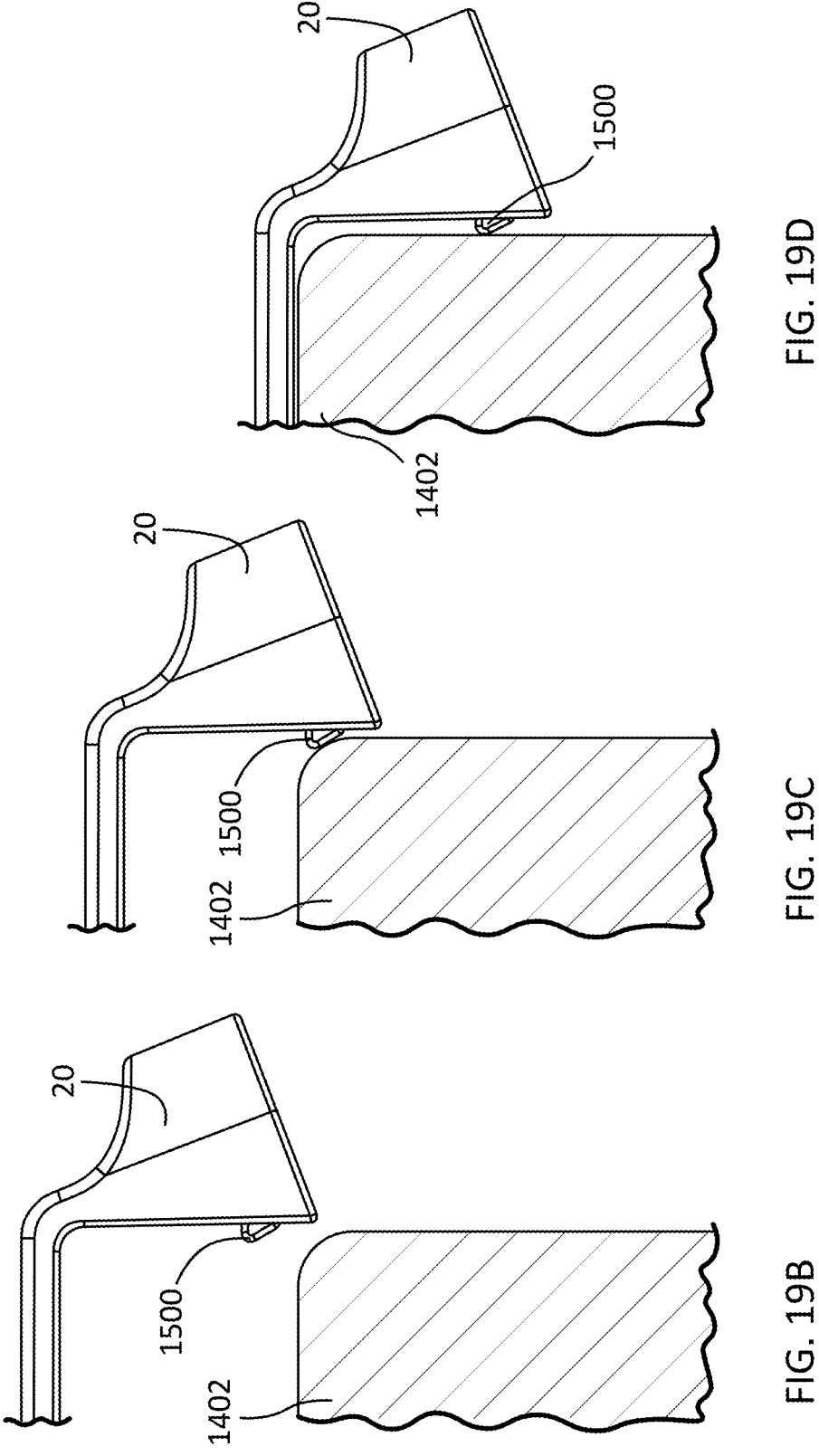
FIG. 19B-19D are sequential side views of the device of FIG. 19A being mounted to a toilet rim.
Figures 20A, 20B:
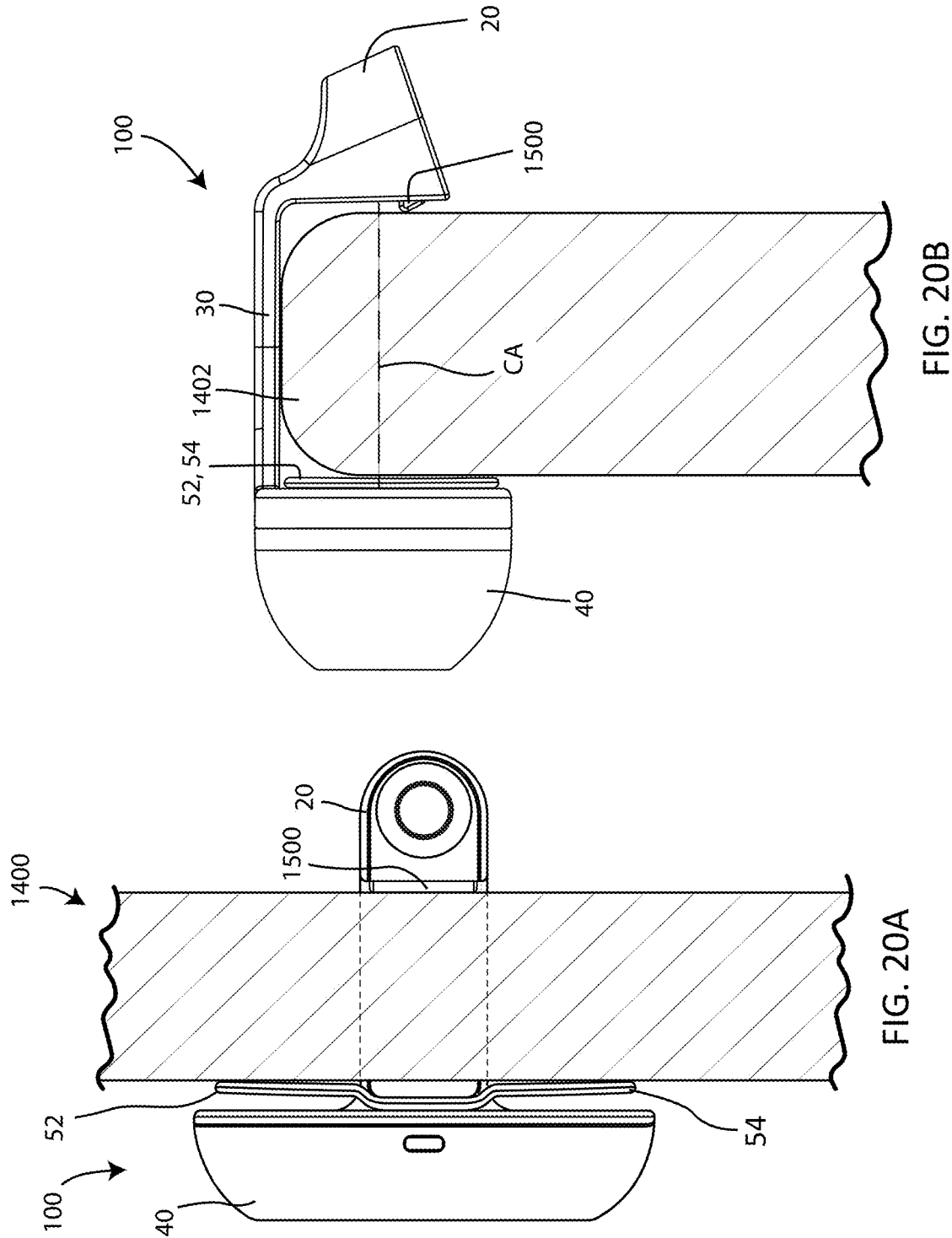
FIGS. 20A and 20B are bottom and side sectional views, respectively, of the device of FIG. 19 mounted to a toilet rim.

In addition, another embodiment of the device may further comprise a protrusion 1500 (FIGS. 19-20) to provide enhanced friction to retain the device when installed. Embodiments of the protrusion 1500 may be located on the rear body 20, such as opposite the attachment arms 52, 54. The protrusion 1500 can be located below a centerline apex CA (FIG. 20B) of the attachment arms 52, 54. In one version, the protrusion 1500 comprises silicone and it is fastened to the rear body 20. Embodiments of the protrusion 1500 can comprise a triangular prism shape with a hypotenuse side 1502 sloped upward with a rounded corner edge 1504.

Further non-limiting examples and embodiments of the present invention are disclosed in the following numbered clauses.

1. A device configured to be mounted to a rim of a bowl of a toilet, the device comprising:
    a front body configured to be located on an exterior of the bowl;
    a rear body configured to be located in an interior of the bowl;
    a bridge that couples the front body to the rear body at a fixed distance therebetween such that the device, when mounted, is configured to straddle the rim; and
    a flexible member located between the front body and the rear body, and the flexible member is configured to adaptably accommodate a width of the rim that is less than the fixed distance to define a device width, to removably secure and retain the device on the rim.

2. The device wherein the fixed distance is not adjustable and the device width is adjustable, via the flexible member, to accommodate a range of rim widths from about 1 inch to about 2.5 inches.

3. The device wherein the device is configured to releasably clamp the rim and be retained on the rim without fasteners.

4. The device wherein the rear body comprises an image capture apparatus.

5. The device wherein the bridge comprises an underside flat that, when mounted, is configured to lay flat on top of the rim.

6. The device wherein a backside of the front body and a front side of the rear body are parallel to each other.

7. The device wherein the bridge is perpendicular to the backside and the front side.

8. The device wherein the flexible member comprises a contoured edge that allows the flexible member to slide and move away from the rim as the device is pushed down onto the rim.

9. The device wherein the contoured edge is semi-circular and provides a lead in or sloped entrance when the device is installed on the rim.

10. The device wherein the flexible member is bonded to and extends from a backside of the front body.

11. The device wherein the flexible member comprises a cantilevered fin that is pliable and hingedly mounted to the front body.

12. The device wherein the flexible member comprises a cantilevered fin that is rigid and hingedly mounted to the front body.

13. The device wherein the flexible member comprises two cantilevered fins that are diagonal to the front body and extend in different directions.

14. The device wherein an angle is defined between the two cantilevered fins and, in an undeformed configuration, the angle is less than 90 degrees and, in a deformed configuration, the angle is greater than 90 degrees.

15. The device wherein the flexible member comprises two pairs of cantilevered fins that are diagonal to the front body and the rear body, respectively, and the cantilevered fins extend in different directions.

16. The device wherein the flexible member comprises only one cantilevered fin that extends from one of the front and rear bodies, and the only one cantilevered fin is substantially perpendicular to said one of the front and rear bodies.

17. The device wherein the flexible member is configured to flexibly interface with an outer side of the bowl.

18. The device wherein the device is configured to be located between the rim and a seat of the toilet.

19. The device wherein the device is configured to not make contact with the seat.

20. The device further comprising a protrusion opposite the flexible member, and the protrusion is located below a centerline apex of the flexible member.

21. The device wherein the protrusion has a triangular prism shape with a hypotenuse side sloped upward with a rounded corner edge 22. A device configured to be mounted to a rim of a bowl of a toilet, the device comprising:
   a front body configured to be located on an exterior of the bowl;
   a rear body configured to be located in an interior of the bowl;
   a bridge that couples the front body to the rear body at a fixed distance therebetween such that the device, when mounted, is configured to straddle the rim; and
   two cantilevered fins located between the front body and the rear body, the two cantilevered fins are configured to adaptably accommodate a width of the rim that is less than the fixed distance to define a device width, to removably secure and retain the device on the rim; and
   an image capture apparatus coupled to the device.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, privacy, etc. As such, to the extent any embodiments are described as less desirable than other embodiments or prior art implementations with respect to one or more characteristics, these embodiments are not outside the scope of the disclosure and can be desirable for particular applications.

What is claimed is:

1. A device configured to be mounted to a rim of a bowl of a toilet, the device comprising:
   a front body configured to be located on an exterior of the bowl;
   a rear body configured to be located in an interior of the bowl;
   a bridge that couples the front body to the rear body at a fixed distance therebetween such that the device, when mounted, is configured to straddle the rim; and
   a flexible member located between the front body and the rear body, wherein the flexible member includes a pair of cantilevered fins extending diagonally from the front body toward the rear body, the pair of cantilevered fins configured to deflect to adaptably accommodate a width of the rim that is less than the fixed distance to define a device width, to removably secure and retain the device on the rim.

2. The device of claim 1, wherein the fixed distance is not adjustable and the device width is adjustable, via the flexible member, to accommodate a range of rim widths from about 1 inch to about 2.5 inches.

3. The device of claim 1, wherein the device is configured to releasably clamp the rim between the pair of cantilevered fins and the rear body such that the device is retained on the rim without additional fasteners.

4. The device of claim 1, wherein the rear body comprises an image capture apparatus.

5. The device of claim 1, wherein the bridge comprises an underside flat that, when mounted, is configured to lay flat on top of the rim.

6. The device of claim 1, wherein a backside of the front body and a front side of the rear body are parallel to each other.

7. The device of claim 6, wherein the bridge is perpendicular to the backside and the front side.

8. The device of claim 1, wherein the flexible member comprises a contoured edge on each of the pair of cantilevered fins that causes the flexible member to deflect away from the rim as the device is pushed down onto the rim.

9. The device of claim 8, wherein the contoured edge is semi-circular and provides a lead in or sloped entrance when the device is installed on the rim.

10. The device of claim 1, wherein the flexible member is bonded to and extends from a backside of the front body.

11. The device of claim 1, wherein the pair of cantilevered fins are pliable and hingedly mounted to the front body.

12. The device of claim 1, wherein the pair of cantilevered fins are rigid and hingedly mounted to the front body.

13. The device of claim 1, wherein the flexible member comprises one or more additional cantilevered fins that extend diagonally from the front body.

14. The device of claim 1, wherein an angle is defined between the pair of cantilevered fins and, in an undeformed configuration, the angle is less than 90 degrees and, in a deformed configuration, the angle is greater than 90 degrees.

15. The device of claim 1, wherein the flexible member comprises two pairs of cantilevered fins that are diagonal to the front body and the rear body, respectively, and the cantilevered fins extend in different directions.

16. The device of claim 1, further comprising a single cantilevered fin that extends from the rear body, the single cantilevered fin substantially perpendicular to the rear body.

17. The device of claim 1, wherein the flexible member is configured to flexibly interface with an outer side of the bowl.

18. The device of claim 1, wherein the bridge of the device is configured to be located between the rim and a seat of the toilet.

19. The device of claim 18, wherein the device is configured to not make contact with the seat.

20. The device of claim 1, further comprising a protrusion opposite the flexible member, wherein the protrusion is located below a centerline apex of the flexible member.

21. The device of claim 20, wherein the protrusion has a triangular prism shape with a hypotenuse side sloped upward with a rounded corner edge.

22. A device configured to be mounted to a rim of a bowl of a toilet, the device comprising:

a front body configured to be located on an exterior of the bowl;

a rear body configured to be located in an interior of the bowl;

a bridge that couples the front body to the rear body at a fixed distance therebetween such that the device, when mounted, is configured to straddle the rim;

a pair of cantilevered fins extending diagonally from the front body toward the rear body, the pair of cantilevered fins configured to deflect to adaptably accommodate a width of the rim that is less than the fixed distance to define a device width, to removably secure and retain the device on the rim; and an image capture apparatus coupled to the device.

* * * * *